US011802131B2

(12) United States Patent
Norcross et al.

(10) Patent No.: US 11,802,131 B2
(45) Date of Patent: Oct. 31, 2023

(54) GLUTARIMIDES FOR MEDICAL TREATMENT

(71) Applicant: C4 Therapeutics, Inc., Watertown, MA (US)

(72) Inventors: Roger Norcross, Basel (CH); Annick Goergler, Basel (CH); Philipp Schmid, Basel (CH); Fabian Dey, Basal (CH); Eric Andre Kusznir, Basel (CH)

(73) Assignee: C4 Therapeutics, Inc., Watertown, MA (US)

( * ) Notice: Subject to any disclaimer, the term of this patent is extended or adjusted under 35 U.S.C. 154(b) by 0 days.

(21) Appl. No.: 16/809,336

(22) Filed: Mar. 4, 2020

(65) Prior Publication Data

US 2020/0207783 A1 Jul. 2, 2020

Related U.S. Application Data

(63) Continuation of application No. PCT/EP2018/073578, filed on Sep. 3, 2018.

(30) Foreign Application Priority Data

Sep. 4, 2017 (EP) .................................. 17189231

(51) Int. Cl.
| C07D 211/88 | (2006.01) |
| A61K 31/437 | (2006.01) |
| C07D 495/14 | (2006.01) |
| C07D 401/12 | (2006.01) |
| C07D 405/12 | (2006.01) |
| C07D 409/12 | (2006.01) |
| C07D 471/04 | (2006.01) |
| C07D 487/04 | (2006.01) |

(52) U.S. Cl.
CPC .......... *C07D 495/14* (2013.01); *C07D 211/88* (2013.01); *C07D 401/12* (2013.01); *C07D 405/12* (2013.01); *C07D 409/12* (2013.01); *C07D 471/04* (2013.01); *C07D 487/04* (2013.01)

(58) Field of Classification Search
None
See application file for complete search history.

(56) References Cited

U.S. PATENT DOCUMENTS

| 4,558,057 A | 12/1985 | Burzynski |
| 5,635,517 A | 6/1997 | Muller et al. |
| 6,306,663 B1 | 10/2001 | Kenten et al. |
| 7,041,298 B2 | 5/2006 | Deshaies et al. |
| 7,208,157 B2 | 4/2007 | Deshaies et al. |
| 9,125,915 B2 | 9/2015 | Miyoshi et al. |
| 9,249,161 B2 | 2/2016 | Albrecht et al. |
| 10,646,575 B2 | 5/2020 | Phillips et al. |
| 10,660,968 B2 | 5/2020 | Phillips et al. |
| 10,849,982 B2 | 12/2020 | Phillips et al. |
| 10,905,768 B1 | 2/2021 | Phillips et al. |
| 11,185,592 B2 | 11/2021 | Phillips et al. |
| 11,254,672 B2 | 2/2022 | Norcross et al. |
| 11,401,256 B2 | 8/2022 | Norcross et al. |
| 11,407,732 B1 | 8/2022 | Henderson et al. |
| 11,459,335 B2 | 10/2022 | Phillips et al. |
| 11,524,949 B2 | 12/2022 | Phillips et al. |
| 11,584,748 B2 | 2/2023 | Nasveschuk et al. |
| 11,623,929 B2 | 4/2023 | Nasveschuk et al. |
| 2013/0190340 A1 | 7/2013 | Hedstrom et al. |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0274738 A1 | 10/2015 | Gray et al. |
| 2015/0291562 A1 | 10/2015 | Crew et al. |
| 2016/0016966 A1 | 1/2016 | Amans et al. |
| 2016/0022642 A1 | 1/2016 | Crews et al. |
| 2016/0045607 A1 | 2/2016 | Crew et al. |
| 2016/0046661 A1 | 2/2016 | Gray et al. |
| 2016/0058872 A1 | 3/2016 | Crew et al. |
| 2016/0176916 A1 | 6/2016 | Bradner et al. |
| 2016/0214972 A1 | 7/2016 | Jin et al. |
| 2016/0272639 A1 | 9/2016 | Crew et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2018/0015087 A1 | 1/2018 | Liu et al. |
| 2018/0085465 A1 | 3/2018 | Bradner et al. |
| 2019/0076539 A1 | 3/2019 | Phillips et al. |

(Continued)

FOREIGN PATENT DOCUMENTS

| BR | PI1100318 A2 | 5/2013 |
| CN | 1696127 A | 11/2005 |

(Continued)

OTHER PUBLICATIONS

Database Registry Chemical Abstracts Service, Columbus, Ohio, Accession No. RN 1463830-80-9, Entered STN: Oct. 25, 2013.*
Database Registry Chemical Abstracts Service, Columbus, Ohio, Accession No. RN 1487722-61-1, Entered STN: Dec. 5, 2013.*
Database Registry Chemical Abstracts Service, Columbus, Ohio, Accession No. RN 1462942-69-3, Entered STN: Oct. 23, 2013.*
Database Registry Chemical Abstracts Service, Columbus, Ohio, Accession No. RN 1957941-94-4, Entered STN: Jul. 22, 2016.*
Database registry chemical abstracts service, Sep. 4, 2011, STN database accession No. 108929-54-0.
Database registry chemical abstracts service, Sep. 4, 2011, STN database accession No. 145931-74-4.

(Continued)

*Primary Examiner* — Samantha L Shterengarts
(74) *Attorney, Agent, or Firm* — Knowles Intellectual Property Strategies, LLC

(57) ABSTRACT

The present invention provides selected glutarimides which bind to the ubiquitously expressed E3 ligase protein cereblon (CRBN) and alter the substrate specificity of the CRBN E3 ubiquitin ligase complex, resulting in breakdown of intrinsic downstream proteins. The disclosed compounds are useful for the treatment of cancer.

9 Claims, No Drawings

(56) References Cited

U.S. PATENT DOCUMENTS

| | | |
|---|---|---|
| 2019/0076542 A1 | 3/2019 | Phillips et al. |
| 2020/0140456 A1 | 5/2020 | Phillips et al. |
| 2020/0207733 A1 | 7/2020 | Norcross et al. |
| 2020/0207764 A1 | 7/2020 | Norcross et al. |
| 2020/0308171 A1 | 10/2020 | Jaeschke et al. |
| 2020/0361930 A1 | 11/2020 | Duplessis et al. |
| 2021/0009559 A1 | 1/2021 | Henderson et al. |
| 2021/0032245 A1 | 2/2021 | Nasveschuk et al. |
| 2021/0070763 A1 | 3/2021 | Nasveschuk et al. |
| 2021/0198256 A1 | 7/2021 | Nasveschuk et al. |
| 2022/0098194 A1 | 3/2022 | Nasveschuk et al. |
| 2022/0289738 A1 | 9/2022 | Norcross et al. |
| 2022/0313826 A1 | 10/2022 | Phillips et al. |
| 2022/0313827 A1 | 10/2022 | Phillips et al. |
| 2022/0372016 A1 | 11/2022 | Phillips et al. |
| 2023/0014124 A1 | 1/2023 | Phillips et al. |
| 2023/0019060 A1 | 1/2023 | Nasveschuk et al. |
| 2023/0082430 A1 | 3/2023 | Henderson et al. |
| 2023/0095223 A1 | 3/2023 | Phillips et al. |
| 2023/0145336 A1 | 5/2023 | Nasveschuk et al. |

FOREIGN PATENT DOCUMENTS

| | | |
|---|---|---|
| CN | 103421061 A | 12/2013 |
| WO | WO 1998/011111 A1 | 3/1998 |
| WO | WO 2002/059106 A1 | 8/2002 |
| WO | WO 2006/102557 A2 | 9/2006 |
| WO | WO 2008/007979 A1 | 1/2008 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2008/122038 A1 | 10/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2011/097218 A1 | 8/2011 |
| WO | WO 2011/143 669 A2 | 11/2011 |
| WO | WO 2012/079022 A1 | 6/2012 |
| WO | WO 2012/178208 A2 | 12/2012 |
| WO | WO 2013/020557 A1 | 2/2013 |
| WO | WO 2013/059215 A1 | 4/2013 |
| WO | WO 2013/063560 A2 | 5/2013 |
| WO | WO 2013/106643 A2 | 7/2013 |
| WO | WO 2013/106646 A2 | 7/2013 |
| WO | WO 2013/170147 A1 | 11/2013 |
| WO | WO 2014/145887 A1 | 9/2014 |
| WO | WO 2015/160845 A2 | 10/2015 |
| WO | WO 2016/011906 A1 | 1/2016 |
| WO | WO 2016/065139 A1 | 4/2016 |
| WO | WO 2016/105518 A1 | 6/2016 |
| WO | WO 2016/146985 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/079267 A1 | 5/2017 |
| WO | WO 2017/117473 A1 | 7/2017 |
| WO | WO 2017/161119 A1 | 9/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/197051 A1 | 11/2017 |
| WO | WO 2017/197240 A1 | 11/2017 |
| WO | WO 2017/201069 A1 | 11/2017 |
| WO | WO 2017/201449 A1 | 11/2017 |
| WO | WO 2018/023 029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |
| WO | WO 2020/0006233 A1 | 1/2020 |

OTHER PUBLICATIONS

Database registry chemical abstracts service, Sep. 4, 2011, STN database accession No. 158828-58-1.

Database registry chemical abstracts service, Sep. 4, 2011, STN database accession No. 158828-61-6.

Database registry chemical abstracts service, Sep. 4, 2011, STN database accession No. 158828-64-9.

Huang Junqin et al., "Chemical modification of antineoplastron A10 and antitumor acticity of its analogs", Zhongguo Yiyao Gongye Zazhi, 1993, 24(10), 437-441, XP002778549; Abstract.

International Written Opinion for PCT/EP2018/073578 dated Mar. 7, 2019.

Agafonov Roman et al., Poster Presentation titled "Quantitative and high throughput method for measuring complex formation between target proteins and E3 ubiquitin ligase", EMBO, Sep. 16, 2017.

Bartlett, et al. "The evolution of thalidomide and its IMiD derivatives as anticancer agents." Nat Rev Cancer 2004, 4(4):312-322.

Berndsen et al. "New insights into ubiquitin E3 ligase mechanism" Nat. Struct. Mol. Biol. 2014, 21:301-307.

Bondeson et al. "Catalytic in vivo protein knockdown by small-molecule PROTACs" Nature Chemical Biology 2015, 11:611-617.

Buckley et al. "HaloPROTACs: Use of Small Molecule PROTACS to Induce Degradation of HaloTag Fusion Proteins" ACS Chemical Biology 2015, 10:1831-1837.

Buckley et al. "Small-Molecule Control of Intracellular Protein Levels through Modulation of the Ubiquitin Proteasome System" Angewandte Reviews, 2014, 53:2312-2330.

Buckley et al. "Targeting the Von Hippel-Lindau E3 Ubiquitin Ligase Using Small Molecules to Disrupt the Vhl/Hif-1alpha Interaction" J. Am. Chem. Soc. 2012, 134:4465-4468.

Buckner et al., "Phase II study of antineoplastons A10 (NSC 648539) and AS2-1 (NSC620261) in patients with recurrent glioma", Mayo Clinic Proceedings, Dowden Health Media, Inc, USA, 1999, 74(2), 137-145.

Burkhard et al. "Synthesis and Stability of Oxetane Analogs of Thalidomide and Lenalidomide" Organic Letters 2013, 15(7):4312-4315.

Chamberlain et al. "Structure of the human cereblon-DDB1-lenalidomide complex reveals basis for responsiveness to thalidomide analogs" Nature Structural and Molecule Biology, 2014, 21(9):803-809.

Chang, X. and Stewart, K. A. "What is the functional role of the thalidomide binding protein cereblon?" Int J Biochem Mol Bio. 2011, 2(3):287-294.

Collins et al., "Chemical approaches to targeted protein degradation through modulation of the ubiquitin-protease pathway", Biochem. J. 2017, 474(7), 1127-1147.

Contino-Pepin, et al., "Preliminary biological evaluations of new thalidomide analogus for multiple sclerosis application", Bioorganic & Medicinal Chemistry Letters, 2009, 19, 878-881.

Corson et al. "Design and applications of bifunctional small molecules: Why two heads are better than one" ACS Chemical Biology 2008, 3(11): 677-692.

(56) References Cited

OTHER PUBLICATIONS

Crew, C. M. "Targeting the undruggable proteome: the small molecules of my dreams" Chemistry and Biology 2010, 17(6):551-555.
Deshaies et al. "Ring domain E3 ubiquitin ligases." Ann. Rev. Biochem. 2009, 78:399-434.
Elam W.A., et al., Poster Presentation titled "Application of Biophysical Techniques to the Targeted Protein Degradation Therapeutic Strategy", Sep. 24, 2017.
Faden et al. "Generic tools for conditionally altering protein abundance and phenotypes on demain" Biol. Chem. 2014, 395(7-8):737-762.
Fisher et al., "Targeted protein degradation and the enzymology of degraders", Current Opinion of Chemical Biology, 2018, 44, 47-55.
Fischer et al. +O2967:P2986"Structure of the DDB1-CRBN E3 ubiquitin ligase in complex with thalidomide" Nature 2014, 512:49-53.
Fischer et al. "The Molecular Basis of CRL4DDB2/CSA Ubiquitin Ligase Architecture, Targeting, and Activation," Cell 2011, 147:1024-1039.
Gosink et al. "Redirecting the Specificity of Ubiquitination by Modifying Ubiquitin-Conjugating Enzymes" Proc. Natl. Acad. Sci. USA 1995, 92:9117-9121.
Gustafson et al. "Small-Molecule-Mediated Degradation of the Androgen Receptor through Hydrophobic Tagging" Angewandte Chemie 2015, 54:9659-9662.
Hendry et al., "Stereochemical modelling studies of the interaction of antineoplaston A10 with DNA", Drugs Under Experimental And Clinical Research, 1987, 13 (Suppl. 1 ), 77-81.
Hines et al. "Posttranslational protein knockdown couple to receptor tyrosine kinase activation with phosphoPROTACs" PNAS 2013, 110(22):8942-8947.
Huang et al., "Chemical modification of antineoplaston A10 and antitumor activity of its analogs", Zhongguo Yiyao Gongye Zazhi, 1993, 24(10), 437-41, 451.
International search report and Written Opinion for PCT/EP2018/073578 dated Jan. 21, 2019.
Invitation to pay additional fees for PCT/EP2018/073578 dated Nov. 29, 2018.
Ito et al. "Identification of a Primary Target of Thalidomide Teratogenicity" Science 2010, 327(5971):1345-1350.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16), 5820-5826.
Jacques et al. "Differentiation of anti-inflammatory and antitumorigenic properties of stabilized enantiomers of thalidomide analogs" PNAS 2015, 112:E1471-E1479.
Kronke et al. "Lenalidomide Causes Selective Degradation of IKZF1 and IKZF3 in Multiple Myeloma Cells" Science 2014, 343(6168):301-305.
Kronke et al. "Lenalidomide induces ubiquitination and degradation of CDK1 [alpha] in del(5q) MDS" Nature 2015, 523(7559):183-188.
Lai et al. "Modular PROTAC Design for the Degradation of Oncogenic BCR-ABL" Angewandte Chemie International Edition 2016, 55:807-810.
Lee et al. "Targeted Degradation of the Aryl Hydrocarbon Receptor by the PROTAC Approach: A Useful Chemical Genetic Tool" ChemBioChem 2007, 8:2058-2062.
Li et al. "Genome-wide and functional annotation of human E3 ubiquitin ligases identifies MULAN, a mitochondrial E3 that regulates the organelle's dynamics and signaling" PLOS One 2008, 3:1487.
Liu et al. "Design and biological characterization of hybrid compounds of curcumin and thalidomide for multiple myeloma" Organic and Biomolecular Chemistry 2013, 11:4757.
Lu et al. "Hijacking the E3 Ubiquitin Ligase Cereblon to Efficiently Target BRD4" Chemistry and Biology 2015, 22(6):755-763.
Lu et al. "The myeloma drug lenalidomide promotes the cereblon-dependent destruction of Ikaros proteins" Science 2014, 343:305-309.
Nasveschuk C., Presentation titled "Advances in the Medicinal Chemistry of Targeted Protein Degradation", Aug. 7, 2018.
Nawaz et al. "Proteasome-Dependent Degradation of the Human Estrogen Receptor" Proc. Natl. Acad. Sci. USA 1999, 96:1858-1862.
Neklesa et al. "Small-molecule hydrophobic tagging-induced degradation of HaloTag fusion proteins." Nat Chem Biol 2011, 7(8):538-543.
Patel, J., Poster Presentation titled "Diverse Utility of Targeted Protein Degradation at C4 Therapeutics", Sep. 17, 2017.
Phillips A., Presentation titled "Targeted Protein Degradation", Applied Pharmaceutical Chemistry, Cambridge, MA, Apr. 5, 2018.
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.
Sakamoto et al. "Development of Protacs to Target Cancer-Promoting Proteins for Ubiquitination and Degradation" Molecular and Cellular Proteomics 2003, 2(12):1350-1357.
Sakamoto et al. "Protacs: chimeric molecules that target proteins to the Skp1-Cullin-F box complex for ubiquitination and degradation" PNAS 2001, 98(15):8554-8559.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Schneekloth et al. "Targeted Intracellular Protein Degradation Induced by a Small Molecule: En Route to Chemical Proteomics" Bioorganic and Medicinal Chemisty Letters 2008, 18:5904-5908.
Shoji, et al., "Modified DNA Aptamer That Binds the (R)-Isomer of a Thalidomide Derivative with High Enantioselectivity", J. Am. Chem., Soc., 2007, 129, 1456-1464.
Smith et al. "Targeted Intracellular Protein Degradation Induced by a Small Molecule: En Route to Chemical Proteomics" Bioorg. Med. Chem. Lett. 2008, 18(22):5904-5908.
Spratt et al. "RBR E3 ubiquitin ligases: new structures, new insights, new questions." Biochem. 2014, 458:421-437.
Toure et al. "Small-Molecule PROTACs: New Approaches to Protein Degradation" Angewandte Chemie International Edition 2016, 55:1966-1973.
Vassilev et al. "In Vivo Activation of the P53 Pathway by Small-Molecule Antagonists of MDM2" Science 2004, 303:844-848.
Vieux Ellen et al., Poster Presentation titled "Measuring Small Molecule Induced Ubiquitination of Proteins", EMBO, Sep. 18, 2017.
Wang et al. "Roles of F-box proteins in cancer," Nat. Rev. Cancer 2014, 14:233-347.
Winter et al. "Phthalimide conjugation as a strategy for in vivo target protein degradation" Science 2015, 348(6241):1376-1381.
Xu Wenfang et al., "Synthesis and antitumor activity of glutamine derivatives" Zhongguo Yiyao Gongye Zazhi, 1992, 23(6), 255-8.
Zengerle et al. "Selective Small Molecule Induced Degradation of the BET Bromodomain Protein BRD4" ACS Chem. Biol. 2015, 10:1770-1777.
Zhou et al. "Harnessng the Ubiquitination Machinery to Target the Degradation of Specific Cellular Proteins" Molecular Cell 2000, 6:751-756.
Zeid Rhamy Presentation titled "Targeted protein degradation as a novel therapeutic approach", Gordon Research Conference, Jun. 26, 2017.
U.S. Appl. No. 16/872,225, filed May 11, 2020, Phillips et al.
U.S. Appl. No. 16/882,236, filed May 22, 2020, Phillips et al.
U.S. Appl. No. 16/874,475, filed May 15, 2020, Phillips et al.
U.S. Appl. No. 17/031,550, filed Sep. 24, 2020, Henderson et al.
U.S. Appl. No. 17/072,896, filed Oct. 16, 2020, Nasveschuk et al.

(56) References Cited

OTHER PUBLICATIONS

U.S. Appl. No. 17/103,621, filed Nov. 24, 2020, Nasveschuk et al.
U.S. Appl. No. 17/107,781, filed Nov. 30, 2020, Phillips et al.
STN Search Results cited in Chinese Patent Application No. 2018800697197.
U.S. Appl. No. 17/878,753, filed Aug. 1, 2022, Norcross et al.
U.S. Appl. No. 17/901,775, filed Sep. 1, 2022, Nasveschuk et al.
U.S. Appl. No. 17/959,144, filed Oct. 3, 2022, Phillips et al.
U.S. Appl. No. 17/965,569, filed Oct. 13, 2022, Nasveschuk et al.
U.S. Appl. No. 17/843,769, filed Jun. 17, 2022, Nasveschuk et al.
U.S. Appl. No. 18/079,815, filed Dec. 12, 2022, Phillips et al.
U.S. Appl. No. 18/084,380, filed Dec. 19, 2022, Nasveschuk et al.
U.S. Appl. No. 17/465,583, filed Sep. 2, 2021, Nasveschuk et al.
U.S. Appl. No. 17/723,199, filed Apr. 18, 2022, Henderson et al.
U.S. Appl. No. 17/524,558, filed Nov. 11, 2021, Phillips et al.
U.S. Appl. No. 17/164,446, filed Feb. 1, 2021, Phillips et al.
U.S. Appl. No. 18/106,893, filed Feb. 7, 2023, Proia et al.
U.S. Appl. No. 18/100,992, filed Jan. 24, 2023, Nasveschuk et al.
U.S. Appl. No. 18/105,735, filed Feb. 3, 2023, Henderson et al.
U.S. Appl. No. 18/117,978, filed Mar. 6, 2023, Nasveschuk et al.
U.S. Appl. No. 18/134,971, filed Apr. 14, 2023, Nasveschuk et al.
U.S. Appl. No. 18/134,985, filed Apr. 14, 2023, Nasveschuk et al.
U.S. Appl. No. 18/134,990, filed Apr. 14, 2023, Nasveschuk et al.
U.S. Appl. No. 18/144,800, filed May 8, 2023, Nasveschuk et al.
Database 1957941-94-4 Ukrogsyntez Ltd. 5H-Cyclopenta[b]pyridine-7-carboxamide,N(2,6-dioxo-3-piperidinyl-6,7-dihydro XP-00278033, Jul. 22, 2016.
Database 1948185-02-1 Ukrorgsyntez LTD. 2H-1-Benzopyran-4-acetamide, N-(2,6-dioxo-3-piperidinyl)-3,4-dihydro-XP002780334, Jul. 8, 2016.
Database 1541076-23-6 Aurora Fine Chemicals. N-(2,6-dioxo-3-piperidinyl)-1,2,3,4,-tetrahydro-XP002780341, Feb. 10, 2014.
Database 1462942-69-3 Aurora Fine Chemicals. 2H-1-Benzopyran-4-carboxamide, N-(2,6-dioxo-3-piperidinyl)-3,4-dihydro, XP-002780348, Oct. 23, 2013.

\* cited by examiner

GLUTARIMIDES FOR MEDICAL TREATMENT

CROSS-REFERENCE TO RELATED APPLICATIONS

This application is a continuation of International Application No. PCT/EP2018/073578, filed Sep. 3, 2018, which claims the benefit of priority to European Patent Application No. 17189231.8, filed Sep. 4, 2017. The entirety of these applications is hereby incorporated by reference herein for all purposes.

FIELD OF THE INVENTION

The present invention provides compounds which bind to the ubiquitously expressed E3 ligase protein cereblon (CRBN) and alter the substrate specificity of the CRBN E3 ubiquitin ligase complex, resulting in breakdown of intrinsic downstream proteins. Present compounds are thus useful for the treatment of cancer.

BACKGROUND OF THE INVENTION

The field of targeted protein degradation promoted by small molecules has been intensively studied over the last years[1].

Protein degradation plays a role in various cellular functions, i.e. the concentrations of regulatory proteins are adjusted through degradation into small peptides to maintain health and productivity of the cells.

Cereblon is a protein that forms an E3 ubiquitin ligase complex, which ubiquinates various other proteins. Cereblon is known as primary target for anticancer thalidomide analogs. A higher expression of cereblon has been linked to the efficiency of thalidomide analogs in cancer therapy.

In recent years, a few bifunctional compounds have been described as useful modulators of targeted ubiquitination, e.g. WO2013020557[2], WO2013063560[3], WO2013106643[4], WO2015160845[5], WO2016011906[6], WO2016105518[7], WO2017007612[8], WO2017024318[9] and WO2017117473[10].

U.S. Pat. No. 4,558,057[11], CN1696127[12], Buckner et al.[13], Huang et al[14], Xu et al.[15], Hendry et al[16], WO2008007979[17], CAS No. 1491860-78-6[18], CAS No. 1480842-08-7[19], CAS No. 1466257-08-8[20], CAS No. 1465134-13-7[21], CAS No. 1462991-23-6[22], WO2017197051[23], CAS No. 1487722-61-1[24], CAS No. 1925250-20-9[25], CAS No. 1512181-14-4[26], CAS No. 1466882-97-2[27], CAS No. 1468435-76-8[28], CAS No. 1467495-41-5[29], CAS No. 1480018-59-4[30], CAS No. 1496032-76-8[31], CAS No. 1993422-50-6[32], CAS No. 1869440-20-9[33], CAS No. 1495663-98-3[34], CAS No. 1491860-78-6[35], CAS No. 1485498-58-5[36], CAS No. 1702002-20-7[37], CAS No. 1490092-27[38], CAS No. 1540138-47-3[39], CAS No. 1998850-87-5[40], CAS No. 1966549-05-2[41], CAS No. 1957941-94-4[42], CAS No. 1948185-02-1[43], CAS No. 1925097-89-7[44], CAS No. 1922676-64-9[45], CAS No. 1923778-80-6[46], CAS No. 1560748-55-1[47], CAS No. 1559709-03-3[48], CAS No. 1543949-70-7[49], CAS No. 1541076-23-6[50], CAS No. 1522124-94-2[51], CAS No. 1519516-43-8[52], CAS No. 1492524-17-0[53], CAS No. 1491481-66-3[54], CAS No. 1486311-15-2[55], CAS No. 1467658-22-5[56], CAS No. 1462942-69-3[57], CAS No. 1464846-46-5[58], and CAS No. 1466763-16-5[59] describe certain structurally similar compounds.

However, there is still an ongoing need for effective treatment of cancers.

SUMMARY OF THE INVENTION

The present invention provides glutarimides of formula I, or a pharmaceutically acceptable salt thereof,

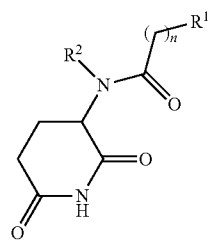

I wherein the substituents and variables are as described below and in the claims, or a pharmaceutically acceptable salt thereof.

The present compounds are useful for the therapeutic and/or prophylactic treatment of cancer.

The compounds of present invention can further be used as part of bifunctional compounds that comprise the compounds of present invention as E3 Ubiquitin Ligase moiety that is linked to a moiety that binds to a target protein where the target protein is proximate to the ubiquitin ligase to effect degradation of said protein.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of cancer.

The following definitions of the general terms used in the present description apply irrespectively of whether the terms in question appear alone or in combination with other groups.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. A specific group is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-}$ $_6$-alkyl and a particular "halogen-C$_{1-3}$-alkyl" is fluoro-C$_{1-3}$-alkyl. Examples are trifluoromethyl, difluoromethyl, fluoromethyl and the like.

The term "hydroxy-C$_{1-6}$-alkyl", alone or in combination with other groups, refers to C$_{1-6}$-alkyl as defined herein, which is substituted by one or multiple hydroxy, particularly by 1 hydroxy. Examples are —CH$_2$OH, —CH$_2$CH$_2$OH and the like.

The term "hydroxy", alone or in combination with other groups, refers to OH.

The term "halogen", alone or in combination with other groups, denotes chloro (Cl), iodo (I), fluoro (F) and bromo (Br). A specific group is F.

The term "heteroaryl" denotes a monovalent heterocyclic mono- or bicyclic ring system of 5 to 12 ring atoms, comprising 1, 2, 3 or 4 heteroatoms selected from N, O and S, the remaining ring atoms being carbon and in which at least one ring is aromatic. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolinyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, dihydroquinolyl, dihydropyrrolopyridinyl, dihydronaphthyridinyl, chromanyl, tetrahydroquinolinyl, dihydrocyclopentapyridinyl quinazolinyl, or quinoxalinyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl.

The term "C$_{1-6}$-alkoxy", alone or in combination with other groups, stands for an —O—C$_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "C$_{1-6}$-alkoxy" are groups with 1 to 4 carbon atoms. A specific group is methoxy.

The term "aryl" denotes a monovalent aromatic carbocyclic mono- or bicyclic ring system comprising 6 to 10 carbon ring atoms and in which at least one ring is aromatic. Examples of aryl moieties include phenyl (Ph), indanyl, tetralinyl and naphthyl. Specific "aryl" is phenyl.

Terms like "a-b-x substituted by R" means that the "x" portion of the moiety is substituted by R.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2$^{nd}$ Edition, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

E1 One embodiment of the invention provides a compound of formula I, or a pharmaceutically acceptable salt thereof,

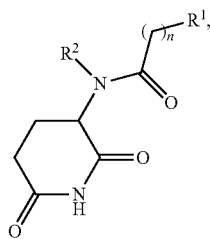

I wherein
$R^1$ is selected from the group consisting of
  i) aryl, optionally substituted by one or more $R^3$,
  ii) heterocycloalkyl, optionally substituted by one or more $R^4$,
  iii) cycloalkyl, optionally substituted by one or more $R^5$, and
  iv) heteroaryl, optionally substituted by one or more $R^6$,
$R^2$ is H, $C_{1-6}$alkyl or —NC(=O)—$C_{1-6}$alkyl,
$R^3$ is H or $C_{1-6}$alkyl,
$R^4$ is H or $C_{1-6}$alkyl,
$R^5$ is H or $C_{1-6}$alkyl,
$R^6$ is H, $C_{1-6}$alkyl, —C(=O)O—$C_{1-6}$alkyl or oxo,
n is 0 or 1;
for use as therapeutically active substance.

E2 A certain embodiment of the invention relates to the compound of formula I, or pharmaceutically acceptable salts thereof, for use as therapeutically active substance, wherein R1 is a carbocycle.

E3 A certain embodiment of the invention relates to the compound of formula I, or pharmaceutically acceptable salts thereof, for use as therapeutically active substance, wherein R1 is a heterocycle.

E4 A certain embodiment of the invention relates to the compound of formula I, or pharmaceutically acceptable salts thereof, wherein
$R^1$ is selected from the group consisting of
  i) aryl, optionally substituted by one or more $R^3$,
  ii) heterocycloalkyl, optionally substituted by one or more $R^4$,
  iii) cycloalkyl, optionally substituted by one or more $R^5$, and
  iv) heteroaryl, optionally substituted by one or more $R^6$,
$R^2$ is H or $C_{1-6}$alkyl,
$R^3$ is H or $C_{1-6}$alkyl,
$R^4$ is H or $C_{1-6}$alkyl,
$R^5$ is H or $C_{1-6}$alkyl,
$R^6$ is H or $C_{1-6}$alkyl,
n is 0 or 1;
for use as therapeutically active substance.

E5 A certain embodiment of the invention relates to the compound of formula I, or pharmaceutically acceptable salts thereof, wherein $R^3$ is selected from the group consisting of
  i) H,
  ii) —C(=O)$C_{1-6}$alkyl
  iii) —C(=O)—N($R^7,R^8$),
  iv) —C(=O)O$C_{1-6}$alkyl,
  v) —$C_{1-6}$alkoxy,
  vi) —$C_{1-6}$alkyl,
  vii) —$C_{1-6}$alkyl-N($R^9$)—C(=O)—$R^{10}$,
  viii) -halogen,
  ix) -halogen-$C_{1-6}$alkyl,
  x) -hydroxy-$C_{1-6}$alkyl,
  xi) —N($R^7,R^8$), and
  xii) —NH—C(=O)$C_{1-6}$alkyl,
wherein $R^7$, $R^8$, $R^9$ and $R^{10}$ are each independently selected from H and $C_{1-6}$alkyl.

E6 A certain embodiment of the invention relates to the compound of formula I, or pharmaceutically acceptable salts thereof, wherein $R^4$ is selected from the group consisting of
  i) H,
  ii) —C(=O)$C_{1-6}$alkyl
  iii) —C(=O)—N($R^7,R^8$),
  iv) —C(=O)O$C_{1-6}$alkyl,
  v) —$C_{1-6}$alkoxy,
  vi) —$C_{1-6}$alkyl,
  vii) —$C_{1-6}$alkyl-N($R^9$)—C(=O)—$R^{10}$,
  viii) -halogen,
  ix) -halogen-$C_{1-6}$alkyl,
  x) -hydroxy-$C_{1-6}$alkyl,
  xi) —N($R^7$,R), and
  xii) —NH—C(=O)$C_{1-6}$alkyl,
wherein $R^7$, $R^8$, $R^9$ and $R^{10}$ are each independently selected from H and $C_{1-6}$alkyl.

E7 A certain embodiment of the invention relates to the compound of formula I, or pharmaceutically acceptable salts thereof, wherein $R^5$ is selected from the group consisting of
  i) H,
  ii) —C(=O)$C_{1-6}$alkyl
  iii) —C(=O)—N($R^7,R^8$),
  iv) —C(=O)O$C_{1-6}$alkyl,
  v) —$C_{1-6}$alkoxy,
  vi) —$C_{1-6}$alkyl,
  vii) —$C_{1-6}$alkyl-N($R^9$)—C(=O)—$R^{10}$,
  viii) -halogen,
  ix) -halogen-$C_{1-6}$alkyl,
  x) -hydroxy-$C_{1-6}$alkyl,
  xi) —N($R^7$,R), and
  xii) —NH—C(=O)$C_{1-6}$alkyl,
wherein $R^7$, $R^8$, $R^9$ and $R^{10}$ are each independently selected from H and $C_{1-6}$alkyl.

E8 A certain embodiment of the invention relates to the compound of formula I, or pharmaceutically acceptable salts thereof, wherein $R^6$ is selected from the group consisting of
  i) H,
  ii) —C(=O)$C_{1-6}$alkyl
  iii) —C(=O)—N($R^7,R^8$),
  iv) —C(=O)O$C_{1-6}$alkyl,
  v) —$C_{1-6}$alkoxy,
  vi) —$C_{1-6}$alkyl,
  vii) —$C_{1-6}$alkyl-N($R^9$)—C(=O)—$R^{10}$,
  viii) -halogen,
  ix) -halogen-$C_{1-6}$alkyl,
  x) -hydroxy-$C_{1-6}$alkyl,
  xi) —N($R^7,R^8$), and
  xii) —NH—C(=O)$C_{1-6}$alkyl, wherein $R^7$, $R^8$, $R^9$ and $R^{10}$ are each independently selected from H and $C_{1-6}$alkyl.

E9 A certain embodiment of the invention relates to the compound of formula I, or pharmaceutically acceptable salts thereof, for use as therapeutically active substance, selected from the group consisting of
(−)-N-((S)-2,6-dioxopiperidin-3-yl)-1,2,3,4-tetrahydroquinoline-4-carboxamide,
(+)-N-((S)-2,6-dioxopiperidin-3-yl)-1,2,3,4-tetrahydroquinoline-4-carboxamide,
(1R)-N-(2,6-dioxo-3-piperidyl)tetralin-1-carboxamide,
(1S)-N-(2,6-dioxo-3-piperidyl)tetralin-1-carboxamide,
(N-((R)-2,6-dioxopiperidin-3-yl)-6,7-dihydro-5H-cyclopenta[b]pyridine-7-carboxamide,
(R)-N-(2,6-dioxopiperidin-3-yl)benzo[b]thiophene-3-carboxamide,
(S)-N-((R)-2,6-dioxopiperidin-3-yl)-1,2,3,4-tetrahydronaphthalene-1-carboxamide,
(S)-N-((S)-2,6-dioxopiperidin-3-yl)-1,2,3,4-tetrahydronaphthalene-1-carboxamide,
(S)-N-(2,6-dioxopiperidin-3-yl)-2,3-dihydro-1H-pyrrolo[2,3-b]pyridine-1-carboxamide,
(S)-N-(2,6-dioxopiperidin-3-yl)-3,4-dihydro-1,8-naphthyridine-1 (2H)-carboxamide,
(S)-N-(2,6-dioxopiperidin-3-yl)-3,4-dihydroquinoline-1 (2H)-carboxamide,
(S)-N-(2,6-dioxopiperidin-3-yl)benzo[b]thiophene-3-carboxamide,
(S)-N-(2,6-dioxopiperidin-3-yl)benzofuran-3-carboxamide,
N-((R)-2,6-dioxopiperidin-3-yl)-6,7-dihydro-5H-cyclopenta[b]pyridine-5-carboxamide,
N-((S)-2,6-dioxopiperidin-3-yl)-6,7-dihydro-5H-cyclopenta[b]pyridine-5-carboxamide,
N-((S)-2,6-dioxopiperidin-3-yl)-6,7-dihydro-5H-cyclopenta[b]pyridine-7-carboxamide,
N-(2,6-dioxo-3-piperidyl)-1H-indole-3-carboxamide,
N-(2,6-dioxo-3-piperidyl)-1-methyl-indole-3-carboxamide,
N-(2,6-dioxo-3-piperidyl)-2-propyl-isoindoline-1-carboxamide,
N-(2,6-dioxo-3-piperidyl)benzamide,
N-(2,6-dioxo-3-piperidyl)benzofuran-3-carboxamide,
N-(2,6-dioxo-3-piperidyl)benzothiophene-3-carboxamide,
N-(2,6-dioxo-3-piperidyl)cyclopentanecarboxamide,
N-(2,6-dioxo-3-piperidyl)indane-1-carboxamide,
N-(2,6-dioxo-3-piperidyl)indane-1-carboxamide,
N-(2,6-dioxo-3-piperidyl)indane-1-carboxamide, isomer A,
N-(2,6-dioxo-3-piperidyl)indane-1-carboxamide, isomer B,
N-(2,6-dioxo-3-piperidyl)indoline-1-carboxamide,
N-(2,6-dioxo-3-piperidyl)-N-methyl-1H-indole-3-carboxamide,
N-[(3R)-2,6-dioxo-3-piperidyl]-1H-indole-3-carboxamide,
N-[(3S)-2,6-dioxo-3-piperidyl]-1H-indole-3-carboxamide,
N-[(3S)-2,6-dioxo-3-piperidyl]-2-phenyl-acetamide, and
N-[(3S)-2,6-dioxo-3-piperidyl]chromane-4-carboxamide.

E10 A certain embodiment of the invention relates to the compound of formula I, or pharmaceutically acceptable salts thereof, wherein
$R^1$ is selected from the group consisting of
i) aryl, optionally substituted by one or more $R^3$,
ii) heterocycloalkyl, optionally substituted by one or more $R^4$,
iii) cycloalkyl, optionally substituted by one or more $R^5$, and
iv) heteroaryl, optionally substituted by one or more $R^6$,
$R^2$ is H or $C_{1-6}$alkyl,
$R^3$ is H or $C_{1-6}$alkyl,
$R^4$ is H or $C_{1-6}$alkyl,
$R^5$ is H or $C_{1-6}$alkyl,
$R^6$ is H or $C_{1-6}$alkyl,
n is 0 or 1;
with the proviso that (1R,2R)-rel-N-(2,6-dioxo-3-piperidinyl)-2-ethyl-cyclopropanecarboxamide, N-(2,6-dioxo-3-piperidinyl)-1,2,3,4-tetrahydro-2-naphthalenecarboxamide, N-(2,6-dioxo-3-piperidinyl)-1-ethyl-cyclopropanecarboxamide, N-(2,6-dioxo-3-piperidinyl)-2,2-dimethyl-cyclopropanecarboxamide, N-(2,6-dioxo-3-piperidinyl)-2,2,3,3-tetramethyl-cyclopropanecarboxamide, N-(2,6-dioxo-3-piperidinyl)-1-methyl-cyclopentanecarboxamide, N-(2,6-dioxo-3-piperidinyl)-cycloheptanecarboxamide, N-(2,6-dioxo-3-piperidinyl)-cyclopropaneacetamide, N-(2,6-dioxo-3-piperidinyl)-cyclopentaneacetamide, N-(2,6-dioxo-3-piperidinyl)-1,2,3,4-tetrahydro-1-naphthalenecarboxamide, N-(2,6-dioxo-3-piperidinyl)-2-methyl-benzeneacetamide, N-(2,6-dioxo-3-piperidinyl)-cyclobutanecarboxamide, 4-butyl-N-(2,6-dioxo-3-piperidinyl)-cyclohexanecarboxamide, N-(2,6-dioxo-3-piperidinyl)-3,4-dimethyl-benzamide, N-(2,6-dioxo-3-piperidinyl)-cyclooctanecarboxamide, 4-(1,1-dimethylethyl)-N-(2,6-dioxo-3-piperidinyl)-benzamide, 2,6-dioxo-3-piperidinyl)-cyclohexaneacetamide, N-(2,6-dioxo-3-piperidinyl)-2,4,6-trimethyl-benzamide, N-(2,6-dioxo-3-piperidinyl)-2,5-dimethyl-benzamide, (3S)-N-(2,6-dioxo-3-piperidinyl)-3-pyrrolidinecarboxamide, N-(2,6-dioxo-3-piperidinyl)-2-methyl-4-piperidinecarboxamide, N-(2,6-dioxo-3-piperidinyl)-6,7-dihydro-5H-cyclopenta[b]pyridine-7-carboxamide, N-(2,6-dioxo-3-piperidinyl)-3,4-dihydro-2H-1-benzopyran-4-acetamide, N-(2,6-dioxo-3-piperidinyl)-2-ethyltetrahydro-3-furancarboxamide, (3R,4R)-rel-N-(2,6-dioxo-3-piperidinyl)-4-methyl-3-pyrrolidinecarboxamide, N-(2,6-dioxo-3-piperidinyl) tetrahydro-3-methyl-2H-pyran-4-carboxamide, N-(2,6-dioxo-3-piperidinyl)-4-methyl-3-pyrrolidinecarboxamide, N-(2,6-dioxo-3-piperidinyl)-2-methyl-3-pyrrolidinecarboxamide, N-(2,6-dioxo-3-piperidinyl)tetrahydro-2H-thiopyran-4-acetamide, N-(2,6-dioxo-3-piperidinyl)-1,2,3,4-tetrahydro-4-quinolinecarboxamide, N-(2,6-dioxo-3-piperidinyl)-4-methyl-1-piperidinecarboxamide, N-(2,6-dioxo-3-piperidinyl)-3-methyl-1-piperidinecarboxamide, N-(2,6-dioxo-3-piperidinyl)-3-pyrrolidineacetamide, N-(2,6-dioxo-3-piperidinyl)-3-azetidineacetamide, N-(2,6-dioxo-3-piperidinyl)-3-azetidinecarboxamide, N-(2,6-dioxo-3-piperidinyl)tetrahydro-2H-pyran-4-carboxamide, N-(2,6-dioxo-3-piperidinyl)tetrahydro-3-furancarboxamide, N-(2,6-dioxo-3-piperidinyl)tetrahydro-3-thiophenecarboxamide, N-(2,6-dioxo-3-piperidinyl)-3,4-dihydro-2H-1-benzopyran-4-carboxamide, N-[(3 S)-2,6-dioxo-3-piperidinyl]-4-methyl-benzamide, N-(2,6-dioxo-3-piperidinyl)-4-methyl-benzeneacetamide, N-(2,6-dioxo-3-piperidinyl)-4-methyl-benzamide, (S)-N-(2,6-dioxo-3-piperidinyl)-1-naphthaleneacetamide, N-[(3S)-2,6-dioxo-3-piperidinyl]-benzamide, N-[(3R)-2,6-dioxo-3-piperidinyl]-benzeneacetamide, N-[(3S)-2,6-dioxo-3-piperidinyl]-benzeneacetamide, N-[(3S)-2,6-dioxo-3-piperidyl]-2-phenyl-acetamide, N-(2,6-dioxo-3-piperidyl)-1H-indole-3-carboxamide, N-(2,6-dioxo-3-piperidyl)-1-methyl-indole-3-carboxamide, N-(2,6-dioxo-3-piperidyl)benzamide, N-(2,6-dioxo-3-piperidyl)cyclopentanecarboxamide, N-(2,6-dioxo-3-piperidyl)benzofuran-3-carboxamide, N-(2,6-dioxo-3-piperidyl)benzothiophene-3-carboxamide, (1R)-N-(2,6-dioxo-3-piperidyl)tetralin-1-carboxamide, (1S)-N-(2,6-dioxo-3-piperidyl)tetralin-1-carboxamide, N-[(3S)-2,6-dioxo-3-piperidyl]-1H-indole-3-carboxamide and N-[(3R)-2,6-dioxo-3-piperidyl]-1H-indole-3-carboxamide are excluded.

E11 A certain embodiment of the invention relates to the compound of formula I, or pharmaceutically acceptable salts thereof,

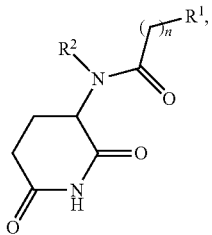

R$^1$ is selected from the group consisting of
i) heterocycloalkyl, optionally substituted by one or more R$^4$,
ii) cycloalkyl, optionally substituted by one or more R$^5$, and
iii) heteroaryl, optionally substituted by one or more R$^6$,
R$^2$ is H or C$_{1-6}$alkyl,
R$^3$ is H or C$_{1-6}$alkyl,
R$^4$ is H or C$_{1-6}$alkyl,
R$^5$ is H or C$_{1-6}$alkyl,
R$^6$ is H or C$_{1-6}$alkyl,
n is 0 or 1;
with the proviso that N-[(3S)-2,6-dioxo-3-piperidyl]-2-phenyl-acetamide, N-(2,6-dioxo-3-piperidyl)-1H-indole-3-carboxamide, N-(2,6-dioxo-3-piperidyl)-1-methyl-indole-3-carboxamide, N-(2,6-dioxo-3-piperidyl)benzamide, N-(2,6-dioxo-3-piperidyl)cyclopentanecarboxamide, N-(2,6-dioxo-3-piperidyl)benzofuran-3-carboxamide, N-(2,6-dioxo-3-piperidyl)benzothiophene-3-carboxamide, (1R)-N-(2,6-dioxo-3-piperidyl)tetralin-1-carboxamide, (1S)-N-(2,6-dioxo-3-piperidyl)tetralin-1-carboxamide, N-[(3S)-2,6-dioxo-3-piperidyl]-1H-indole-3-carboxamide and N-[(3R)-2,6-dioxo-3-piperidyl]-1H-indole-3-carboxamide are excluded.

E12 A certain embodiment of the invention relates to the compound of formula I, or pharmaceutically acceptable salts thereof, wherein R1 is a carbocycle.

E13 A certain embodiment of the invention relates to the compound of formula I, or pharmaceutically acceptable salts thereof, wherein R1 is a heterocycle.

E14 A certain embodiment of the invention relates to the compound of formula I, or pharmaceutically acceptable salts thereof, wherein
n is 0,
R$^1$ is selected from the group consisting of
i) heterocycloalkyl,
ii) cycloalkyl, and
iii) heteroaryl.
R$^2$ is H or C$_{1-6}$alkyl.

E15 A certain embodiment of the invention relates to the compound of formula I, or pharmaceutically acceptable salts thereof, wherein R$^1$ is selected from the group consisting of
i) heterocycloalkyl,
ii) cycloalkyl, and
iii) heteroaryl.

E16 A certain embodiment of the invention relates to the compound of formula I, or pharmaceutically acceptable salts thereof, wherein R$^1$ is selected from the group consisting of i) 1,2,3,4-tetrahydronaphthalenyl,
ii) 1,2,3,4-tetrahydroquinolinyl,
iii) 1H-indolyl,
iv) 1-Me-indolyl,
v) 2,3-dihydro-1H-pyrrolo[2,3-b]pyridinyl,
vi) 3,4-dihydro-1,8-naphthyridinyl,
vii) 3,4-dihydroquinolinyl,
viii) 6,7-dihydro-5H-cyclopenta[b]pyridinyl,
ix) benzo[b]thiophenyl,
x) benzofuranyl,
xi) benzothiophenyl,
xii) chromanyl,
xiii) cyclopentyl,
xiv) indanyl,
xv) indolinyl,
xvi) isoindolinyl, and
xvii) tetralinyl.

E17 A certain embodiment of the invention relates to the compound of formula I, or pharmaceutically acceptable salts thereof, wherein R$^2$ is H.

E18 A certain embodiment of the invention relates to the compound of formula I, or pharmaceutically acceptable salts thereof, wherein R$^6$ is C$_{1-6}$alkyl.

E19 A certain embodiment of the invention relates to the compound of formula I, or pharmaceutically acceptable salts thereof, wherein R$^6$ is Me or propyl.

E20 A certain embodiment of the invention relates to the compound of formula I, or pharmaceutically acceptable salts thereof, selected from the group consisting of
(S)-N-((R)-2,6-dioxopiperidin-3-yl)-1,2,3,4-tetrahydronaphthalene-1-carboxamide,
(S)-N-((S)-2,6-dioxopiperidin-3-yl)-1,2,3,4-tetrahydronaphthalene-1-carboxamide,
(−)-N-((S)-2,6-dioxopiperidin-3-yl)-1,2,3,4-tetrahydroquinoline-4-carboxamide,
(+)-N-((S)-2,6-dioxopiperidin-3-yl)-1,2,3,4-tetrahydroquinoline-4-carboxamide,
N-[(3S)-2,6-dioxo-3-piperidyl]-1,2,3,4-tetrahydroquinoline-4-carboxamide,
N-[(3R)-2,6-dioxo-3-piperidyl]-1,2,3,4-tetrahydroquinoline-4-carboxamide,
(S)-N-((R)-2,6-dioxopiperidin-3-yl)-1,2,3,4-tetrahydroquinoline-4-carboxamide,
(4R)-N-[(3R)-2,6-dioxopiperidin-3-yl]-1,2,3,4-tetrahydroquinoline-4-carboxamide,
(R)-N-((R)-2,6-dioxopiperidin-3-yl)-1,2,3,4-tetrahydronaphthalene-1-carboxamide,
(R)-N-((S)-2,6-dioxopiperidin-3-yl)-1,2,3,4-tetrahydronaphthalene-1-carboxamide,
(1S)-N-(1-methyl-2,6-dioxopiperidin-3-yl)-1,2,3,4-tetrahydronaphthalene-1-carboxamide,
(1S)-N-(1-methyl-2,6-dioxopiperidin-3-yl)-1,2,3,4-tetrahydronaphthalene-1-carboxamide,
(1S)-N-(1-methyl-2,6-dioxopiperidin-3-yl)-1,2,3,4-tetrahydronaphthalene-1-carboxamide,
(S)-N-(2,6-dioxopiperidin-3-yl)-1-methyl-4,5,6,7-tetrahydro-1H-pyrazolo[4,3-c]pyridine-3-carboxamide,
(S)-N-(2,6-dioxopiperidin-3-yl)imidazo[1,2-a]pyridine-3-carboxamide,
(R)-N-(2,6-dioxopiperidin-3-yl)imidazo[1,2-a]pyridine-3-carboxamide,
(S)-N-(2,6-dioxopiperidin-3-yl)-2,3-dihydro-1H-pyrrolo[2,3-b]pyridine-1-carboxamide,
(R)-N-(2,6-dioxopiperidin-3-yl)-2,3-dihydro-1H-pyrrolo[2,3-b]pyridine-1-carboxamide,
N-(2,6-dioxopiperidin-3-yl)-N-methyl-2,3-dihydro-1H-pyrrolo[2,3-b]pyridine-1-carboxamide, N-[(3S)-2,6-dioxo-3-piperidyl]-1-methyl-3,4-dihydro-2H-quinoline-4-carboxamide,
N-[(3R)-2,6-dioxo-3-piperidyl]-1-methyl-3,4-dihydro-2H-quinoline-4-carboxamide,
(S)-N-(2,6-dioxopiperidin-3-yl)-3,4-dihydroquinoline-1(2H)-carboxamide,
(R)-N-(2,6-dioxopiperidin-3-yl)-3,4-dihydroquinoline-1(2H)-carboxamide,
(S)-N-(2,6-dioxopiperidin-3-yl)pyrazolo[1,5-a]pyridine-3-carboxamide,
(R)-N-(2,6-dioxopiperidin-3-yl)pyrazolo[1,5-a]pyridine-3-carboxamide,
(S)-N-(2,6-dioxopiperidin-3-yl)imidazo[1,5-a]pyridine-3-carboxamide,
(R)-N-(2,6-dioxopiperidin-3-yl)imidazo[1,5-a]pyridine-3-carboxamide,
(S)-N-(2,6-dioxopiperidin-3-yl)pyrazolo[1,5-a]pyrimidine-3-carboxamide,
(R)-N-(2,6-dioxopiperidin-3-yl)pyrazolo[1,5-a]pyrimidine-3-carboxamide,
N-[(3S)-2,6-dioxo-3-piperidyl]-2-phenyl-acetamide,
N-(2,6-dioxo-3-piperidyl)indane-1-carboxamide,
N-(2,6-dioxo-3-piperidyl)-2-propyl-isoindoline-1-carboxamide,
N-(2,6-dioxo-3-piperidyl)indane-1-carboxamide, isomer A,
N-(2,6-dioxo-3-piperidyl)indane-1-carboxamide, isomer B,
N-(2,6-dioxo-3-piperidyl)indane-1-carboxamide,
N-(2,6-dioxo-3-piperidyl)-1H-indole-3-carboxamide,
N-(2,6-dioxo-3-piperidyl)-1-methyl-indole-3-carboxamide,
N-(2,6-dioxo-3-piperidyl)indoline-1-carboxamide,
N-(2,6-dioxo-3-piperidyl)benzamide,
N-(2,6-dioxo-3-piperidyl)cyclopentanecarboxamide,
N-(2,6-dioxo-3-piperidyl)benzofuran-3-carboxamide,
N-(2,6-dioxo-3-piperidyl)benzothiophene-3-carboxamide,
(1R)-N-(2,6-dioxo-3-piperidyl)tetralin-1-carboxamide,
(1S)-N-(2,6-dioxo-3-piperidyl)tetralin-1-carboxamide,
N-(2,6-dioxo-3-piperidyl)-N-methyl-1H-indole-3-carboxamide,
N-[(3S)-2,6-dioxo-3-piperidyl]-1H-indole-3-carboxamide,
N-[(3R)-2,6-dioxo-3-piperidyl]-1H-indole-3-carboxamide,
(S)-N-(2,6-dioxopiperidin-3-yl)benzofuran-3-carboxamide,
(R)-N-(2,6-dioxopiperidin-3-yl)benzo[b]thiophene-3-carboxamide,
(S)-N-(2,6-dioxopiperidin-3-yl)benzo[b]thiophene-3-carboxamide,
N-[(3S)-2,6-dioxo-3-piperidyl]chromane-4-carboxamide,
(R)-N-(2,6-dioxopiperidin-3-yl)benzofuran-3-carboxamide,
N-[(3R)-2,6-dioxo-3-piperidyl]chromane-4-carboxamide,
methyl (S)-3-((2,6-dioxopiperidin-3-yl)carbamoyl)-1H-indole-6-carboxylate,
(R)-N-(2,6-dioxopiperidin-3-yl)-1H-indazole-3-carboxamide,
(S)-N-(2,6-dioxopiperidin-3-yl)indolizine-3-carboxamide,
(R)-N-(2,6-dioxopiperidin-3-yl)indolizine-3-carboxamide,
N-(2,6-dioxopiperidin-3-yl)-N-methylindoline-1-carboxamide,
(S)-N-(2,6-dioxopiperidin-3-yl)-N-methylindoline-1-carboxamide,
(R)-N-(2,6-dioxopiperidin-3-yl)-N-methylindoline-1-carboxamide,
(S)-N-(2,6-dioxopiperidin-3-yl)-2-(pyridin-3-yl)acetamide,
(R)-N-(2,6-dioxopiperidin-3-yl)-2-(pyridin-3-yl)acetamide,
(S)-2-(4-acetamidophenyl)-N-(2,6-dioxopiperidin-3-yl)acetamide,
(R)-2-(4-acetamidophenyl)-N-(2,6-dioxopiperidin-3-yl)acetamide,
(R)-2-(3-acetamidophenyl)-N-(2,6-dioxopiperidin-3-yl)acetamide,
(S)-2-(3-acetamidophenyl)-N-(2,6-dioxopiperidin-3-yl)acetamide,
(S)-N-(2,6-dioxopiperidin-3-yl)-2-(2-oxoindolin-5-yl)acetamide,
(R)-N-(2,6-dioxopiperidin-3-yl)-2-(2-oxoindolin-5-yl)acetamide,
tert-butyl (S)-3-((2,6-dioxopiperidin-3-yl)carbamoyl)-1-methyl-1,4,6,7-tetrahydro-5H-pyrazolo[4,3-c]pyridine-5-carboxylate,
N-((S)-2,6-dioxopiperidin-3-yl)-6,7-dihydro-5H-cyclopenta[b]pyridine-5-carboxamide,
N-((R)-2,6-dioxopiperidin-3-yl)-6,7-dihydro-5H-cyclopenta[b]pyridine-5-carboxamide,
(N-((R)-2,6-dioxopiperidin-3-yl)-6,7-dihydro-5H-cyclopenta[b]pyridine-7-carboxamide,
N-((S)-2,6-dioxopiperidin-3-yl)-6,7-dihydro-5H-cyclopenta[b]pyridine-7-carboxamide,
(S)-N-(2,6-dioxopiperidin-3-yl)-3,4-dihydro-1,8-naphthyridine-1(2H)-carboxamide, and
(R)-N-(2,6-dioxopiperidin-3-yl)-3,4-dihydro-1,8-naphthyridine-1(2H)-carboxamide.

E21 A certain embodiment of the invention relates to the compound of formula I, or pharmaceutically acceptable salts thereof, selected from the group consisting of
(S)-N-((R)-2,6-dioxopiperidin-3-yl)-1,2,3,4-tetrahydronaphthalene-1-carboxamide,
(S)-N-((S)-2,6-dioxopiperidin-3-yl)-1,2,3,4-tetrahydronaphthalene-1-carboxamide,
(−)-N-((S)-2,6-dioxopiperidin-3-yl)-1,2,3,4-tetrahydroquinoline-4-carboxamide,
(+)-N-((S)-2,6-dioxopiperidin-3-yl)-1,2,3,4-tetrahydroquinoline-4-carboxamide,
N-[(3S)-2,6-dioxo-3-piperidyl]-1,2,3,4-tetrahydroquinoline-4-carboxamide,
N-[(3R)-2,6-dioxo-3-piperidyl]-1,2,3,4-tetrahydroquinoline-4-carboxamide,
(S)-N-((R)-2,6-dioxopiperidin-3-yl)-1,2,3,4-tetrahydroquinoline-4-carboxamide,
(4R)-N-[(3R)-2,6-dioxopiperidin-3-yl]-1,2,3,4-tetrahydroquinoline-4-carboxamide,
(R)-N-((R)-2,6-dioxopiperidin-3-yl)-1,2,3,4-tetrahydronaphthalene-1-carboxamide,
(R)-N-((S)-2,6-dioxopiperidin-3-yl)-1,2,3,4-tetrahydronaphthalene-1-carboxamide,
(S)-N-(2,6-dioxopiperidin-3-yl)-1-methyl-4,5,6,7-tetrahydro-1H-pyrazolo[4,3-c]pyridine-3-carboxamide,
(S)-N-(2,6-dioxopiperidin-3-yl)imidazo[1,2-a]pyridine-3-carboxamide,
(R)-N-(2,6-dioxopiperidin-3-yl)imidazo[1,2-a]pyridine-3-carboxamide,
(S)-N-(2,6-dioxopiperidin-3-yl)-2,3-dihydro-1H-pyrrolo[2,3-b]pyridine-1-carboxamide,
(R)-N-(2,6-dioxopiperidin-3-yl)-2,3-dihydro-1H-pyrrolo[2,3-b]pyridine-1-carboxamide,
N-(2,6-dioxopiperidin-3-yl)-N-methyl-2,3-dihydro-1H-pyrrolo[2,3-b]pyridine-1-carboxamide,
N-[(3S)-2,6-dioxo-3-piperidyl]-1-methyl-3,4-dihydro-2H-quinoline-4-carboxamide,
N-[(3R)-2,6-dioxo-3-piperidyl]-1-methyl-3,4-dihydro-2H-quinoline-4-carboxamide,
(S)-N-(2,6-dioxopiperidin-3-yl)-3,4-dihydroquinoline-1(2H)-carboxamide,
(R)-N-(2,6-dioxopiperidin-3-yl)-3,4-dihydroquinoline-1(2H)-carboxamide, (S)-N-(2,6-dioxopiperidin-3-yl)pyrazolo[1,5-a]pyridine-3-carboxamide,
(R)-N-(2,6-dioxopiperidin-3-yl)pyrazolo[1,5-a]pyridine-3-carboxamide,
(S)-N-(2,6-dioxopiperidin-3-yl)imidazo[1,5-a]pyridine-3-carboxamide,
(R)-N-(2,6-dioxopiperidin-3-yl)imidazo[1,5-a]pyridine-3-carboxamide,
(S)-N-(2,6-dioxopiperidin-3-yl)pyrazolo[1,5-a]pyrimidine-3-carboxamide,
(R)-N-(2,6-dioxopiperidin-3-yl)pyrazolo[1,5-a]pyrimidine-3-carboxamide,
N-[(3S)-2,6-dioxo-3-piperidyl]-2-phenyl-acetamide,
N-(2,6-dioxo-3-piperidyl)indane-1-carboxamide,
N-(2,6-dioxo-3-piperidyl)-2-propyl-isoindoline-1-carboxamide,
N-(2,6-dioxo-3-piperidyl)indane-1-carboxamide, isomer A,
N-(2,6-dioxo-3-piperidyl)indane-1-carboxamide, isomer B,
N-(2,6-dioxo-3-piperidyl)indane-1-carboxamide,
N-(2,6-dioxo-3-piperidyl)-1H-indole-3-carboxamide,
N-(2,6-dioxo-3-piperidyl)-1-methyl-indole-3-carboxamide,
N-(2,6-dioxo-3-piperidyl)indoline-1-carboxamide,
N-(2,6-dioxo-3-piperidyl)benzamide,
N-(2,6-dioxo-3-piperidyl)cyclopentanecarboxamide,
N-(2,6-dioxo-3-piperidyl)benzofuran-3-carboxamide,
N-(2,6-dioxo-3-piperidyl)benzothiophene-3-carboxamide,
(1R)-N-(2,6-dioxo-3-piperidyl)tetralin-1-carboxamide,
(1S)-N-(2,6-dioxo-3-piperidyl)tetralin-1-carboxamide,
N-(2,6-dioxo-3-piperidyl)-N-methyl-1H-indole-3-carboxamide,
N-[(3S)-2,6-dioxo-3-piperidyl]-1H-indole-3-carboxamide,
N-[(3R)-2,6-dioxo-3-piperidyl]-1H-indole-3-carboxamide,
(S)-N-(2,6-dioxopiperidin-3-yl)benzofuran-3-carboxamide,
(R)-N-(2,6-dioxopiperidin-3-yl)benzo[b]thiophene-3-carboxamide,
(S)-N-(2,6-dioxopiperidin-3-yl)benzo[b]thiophene-3-carboxamide,
N-[(3S)-2,6-dioxo-3-piperidyl]chromane-4-carboxamide,
(R)-N-(2,6-dioxopiperidin-3-yl)benzofuran-3-carboxamide,
N-[(3R)-2,6-dioxo-3-piperidyl]chromane-4-carboxamide,
methyl (S)-3-((2,6-dioxopiperidin-3-yl)carbamoyl)-1H-indole-6-carboxylate,
(R)-N-(2,6-dioxopiperidin-3-yl)-1H-indazole-3-carboxamide,
(S)-N-(2,6-dioxopiperidin-3-yl)indolizine-3-carboxamide,
(R)-N-(2,6-dioxopiperidin-3-yl)indolizine-3-carboxamide,
N-(2,6-dioxopiperidin-3-yl)-N-methylindoline-1-carboxamide,
(S)-N-(2,6-dioxopiperidin-3-yl)-N-methylindoline-1-carboxamide,
(R)-N-(2,6-dioxopiperidin-3-yl)-N-methylindoline-1-carboxamide,
(S)-N-(2,6-dioxopiperidin-3-yl)-2-(pyridin-3-yl)acetamide,
(R)-N-(2,6-dioxopiperidin-3-yl)-2-(pyridin-3-yl)acetamide,
(S)-2-(4-acetamidophenyl)-N-(2,6-dioxopiperidin-3-yl)acetamide,
(R)-2-(4-acetamidophenyl)-N-(2,6-dioxopiperidin-3-yl)acetamide,
(R)-2-(3-acetamidophenyl)-N-(2,6-dioxopiperidin-3-yl)acetamide,
(S)-2-(3-acetamidophenyl)-N-(2,6-dioxopiperidin-3-yl)acetamide,
(S)-N-(2,6-dioxopiperidin-3-yl)-2-(2-oxoindolin-5-yl)acetamide,
(R)-N-(2,6-dioxopiperidin-3-yl)-2-(2-oxoindolin-5-yl)acetamide,
tert-butyl (S)-3-((2,6-dioxopiperidin-3-yl)carbamoyl)-1-methyl-1,4,6,7-tetrahydro-5H-pyrazolo[4,3-c]pyridine-5-carboxylate,
N-((S)-2,6-dioxopiperidin-3-yl)-6,7-dihydro-5H-cyclopenta[b]pyridine-5-carboxamide,
N-((R)-2,6-dioxopiperidin-3-yl)-6,7-dihydro-5H-cyclopenta[b]pyridine-5-carboxamide,
(N-((R)-2,6-dioxopiperidin-3-yl)-6,7-dihydro-5H-cyclopenta[b]pyridine-7-carboxamide,
N-((S)-2,6-dioxopiperidin-3-yl)-6,7-dihydro-5H-cyclopenta[b]pyridine-7-carboxamide,
(S)-N-(2,6-dioxopiperidin-3-yl)-3,4-dihydro-1,8-naphthyridine-1(2H)-carboxamide, and
(R)-N-(2,6-dioxopiperidin-3-yl)-3,4-dihydro-1,8-naphthyridine-1(2H)-carboxamide.

E22 A certain embodiment of the invention relates to the compound of formula I, or pharmaceutically acceptable salts thereof, selected from the group consisting of
(−)-N-((S)-2,6-dioxopiperidin-3-yl)-1,2,3,4-tetrahydroquinoline-4-carboxamide,
(+)-N-((S)-2,6-dioxopiperidin-3-yl)-1,2,3,4-tetrahydroquinoline-4-carboxamide,
(N-((R)-2,6-dioxopiperidin-3-yl)-6,7-dihydro-5H-cyclopenta[b]pyridine-7-carboxamide,
(R)-N-(2,6-dioxopiperidin-3-yl)benzo[b]thiophene-3-carboxamide,
(S)-N-((R)-2,6-dioxopiperidin-3-yl)-1,2,3,4-tetrahydronaphthalene-1-carboxamide,
(S)-N-((S)-2,6-dioxopiperidin-3-yl)-1,2,3,4-tetrahydronaphthalene-1-carboxamide,
(S)-N-(2,6-dioxopiperidin-3-yl)-2,3-dihydro-1H-pyrrolo[2,3-b]pyridine-1-carboxamide,
(S)-N-(2,6-dioxopiperidin-3-yl)-3,4-dihydro-1,8-naphthyridine-1 (2H)-carboxamide,
(S)-N-(2,6-dioxopiperidin-3-yl)-3,4-dihydroquinoline-1 (2H)-carboxamide,
(S)-N-(2,6-dioxopiperidin-3-yl)benzo[b]thiophene-3-carboxamide,
(S)-N-(2,6-dioxopiperidin-3-yl)benzofuran-3-carboxamide,
N-((R)-2,6-dioxopiperidin-3-yl)-6,7-dihydro-5H-cyclopenta[b]pyridine-5-carboxamide,
N-((S)-2,6-dioxopiperidin-3-yl)-6,7-dihydro-5H-cyclopenta[b]pyridine-5-carboxamide,
N-((S)-2,6-dioxopiperidin-3-yl)-6,7-dihydro-5H-cyclopenta[b]pyridine-7-carboxamide,
N-[(3S)-2,6-dioxo-3-piperidyl]chromane-4-carboxamide,
3-amino-N-methyl-4-[(2-oxo-1,3-dihydrobenzimidazol-5-yl)amino]benzamide,
N-methyl-2-[2-(3-methylimidazol-4-yl)-4-quinolyl]-1-(2-oxo-1,3-dihydrobenzimidazol-5-yl)benzimidazole-5-carboxamide,
N-methyl-1-(2-oxo-1,3-dihydrobenzimidazol-5-yl)-2-(4-quinolyl)benzimidazole-5-carboxamide,
2-ethyl-N-methyl-1-(2-oxo-1,3-dihydrobenzimidazol-5-yl)benzimidazole-5-carboxamide,
N,2-dimethyl-1-(2-oxo-1,3-dihydrobenzimidazol-5-yl)benzimidazole-5-carboxamide,
5-[2-(4-quinolyl)benzimidazol-1-yl]-1,3-dihydrobenzimidazol-2-one,
5-[2-[2-(3-methylimidazol-4-yl)-4-quinolyl]benzimidazol-1-yl]-1,3-dihydrobenzimidazol-2-one,
methyl 3-amino-4-[(2-oxo-1,3-dihydrobenzimidazol-5-yl)amino]benzoate,
N-methyl-1-(2-oxo-1,3-dihydrobenzimidazol-5-yl)-2-phenyl-benzimidazole-5-carboxamide,
N-methyl-1-(2-oxo-1,3-dihydrobenzimidazol-5-yl)-2-(4-pyridyl)benzimidazole-5-carboxamide, N-methyl-1-(2-oxo-1,3-dihydrobenzimidazol-5-yl)-2-(trifluoromethyl)benzimidazole-5-carboxamide,
N-methyl-1-(2-oxo-1,3-dihydrobenzimidazol-5-yl)-2-propyl-benzimidazole-5-carboxamide,
2-(1H-imidazol-5-yl)-N-methyl-1-(2-oxo-1,3-dihydrobenzimidazol-5-yl)benzimidazole-5-carboxamide,
2-isopropyl-N-methyl-1-(2-oxo-1,3-dihydrobenzimidazol-5-yl)benzimidazole-5-carboxamide,
1-(1,3-dimethyl-2-oxo-benzimidazol-5-yl)-N-methyl-2-[2-(3-methylimidazol-4-yl)-4-quinolyl]benzimidazole-5-carboxamide,
N,N-dimethyl-2-[2-(3-methylimidazol-4-yl)-4-quinolyl]-1-(2-oxo-1,3-dihydrobenzimidazol-5-yl)benzimidazole-5-carboxamide,
2-(3-methoxybenzyl)-N-methyl-2'-oxo-2',3'-dihydro-1'H-[1,5'-bibenzo[d]imidazole]-5-carboxamide, and
2-isopropyl-N-methyl-2'-oxo-2',3'-dihydro-1'H-[1,5'-bibenzo[d]imidazole]-6-carboxamide.

E23 A certain embodiment of the invention relates to the compound of formula I, or pharmaceutically acceptable salts thereof, having a chemical structure comprising:

P-L-C wherein
L is a linker group;
C is a compound of formula I according to any one of the embodiments,
wherein L is chemically linked to C; and
P is a protein target moiety that binds to a target protein or a target polypeptide,
wherein L is chemically linked to P.

E24 A certain embodiment of the invention relates to the compound of formula P-L-C, or pharmaceutically acceptable salts thereof, wherein L is selected from the group consisting of:
i) —NHCH$_2$—(CH$_2$)$_{1-30}$—CH$_2$NH—, and
ii) —NH—(CH$_2$CH$_2$O)$_{1-25}$—CH$_2$CH$_2$—NH—.

E25 A certain embodiment of the invention relates to the compound of formula P-L-C, or pharmaceutically acceptable salts thereof, wherein L is selected from the group consisting of:
i) —NHCH$_2$—(CH$_2$)$_{1-10}$—CH$_2$NH—, and
ii) —NH—(CH$_2$CH$_2$O)$_{1-5}$—CH$_2$CH$_2$—NH—.

E26 A certain embodiment of the invention relates to the compound of formula P-L-C, or pharmaceutically acceptable salts thereof, wherein P is a BRD4 inhibitor, in particular wherein P is

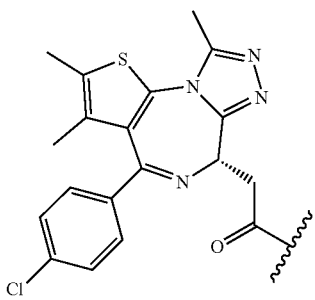 [SMILES: *C(=O)C[C@@H]1N=C(c2ccc(Cl)cc2)c2c(sc(C)c2C)-n2c(C)nnc21]

E27 A certain embodiment of the invention relates to the compound of formula P-L-C, or pharmaceutically acceptable salts thereof, selected from the group consisting of
(4S)-1-[6-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]hexanoyl]-N-[(3R)-2,6-dioxo-3-piperidyl]-3,4-dihydro-2H-quinoline-4-carboxamide,
(4R)-1-[2-[2-[2-[2-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]ethoxy]ethoxy]ethoxy]acetyl]-N-[(3S)-2,6-dioxo-3-piperidyl]-3,4-dihydro-2H-quinoline-4-carboxamid, and
(4S)-1-[6-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]hexanoyl]-N-[(3S)-2,6-dioxo-3-piperidyl]-3,4-dihydro-2H-quinoline-4-carboxamide.

E28 A certain embodiment of the invention relates to the compound of formula I as described herein, or a pharmaceutically acceptable salt thereof, for use as therapeutically active substance.

E29 A certain embodiment of the invention relates to the compound of formula I as described herein, or a pharmaceutically acceptable salt thereof, for the use in the therapeutic and/or prophylactic treatment of cancer.

E30 A certain embodiment of the invention relates to the compound of formula I as described herein, or a pharmaceutically acceptable salt thereof, for the manufacture of a medicament for the therapeutic and/or prophylactic treatment of cancer.

E31 A certain embodiment of the invention relates to a pharmaceutical composition comprising the compound of formula I as described herein, or a pharmaceutically acceptable salt thereof, and a pharmaceutically acceptable auxiliary substance.

E32 A certain embodiment of the invention relates to a method for the therapeutic and/or prophylactic treatment of cancer, by administering the compound of formula I as described herein, or a pharmaceutically acceptable salt thereof, to a patient.

E33 A certain embodiment of the invention relates to the compound of P-L-C as described herein, or a pharmaceutically acceptable salt thereof, for use as therapeutically active substance.

E34 A certain embodiment of the invention relates to the compound of P-L-C as described herein, or a pharmaceutically acceptable salt thereof, for the use in the therapeutic and/or prophylactic treatment of cancer.

E35 A certain embodiment of the invention relates to the compound of P-L-C as described herein, or a pharmaceutically acceptable salt thereof, for the manufacture of a medicament for the therapeutic and/or prophylactic treatment of cancer.

E36 A certain embodiment of the invention relates to a pharmaceutical composition comprising the compound of P-L-C as described herein, or a pharmaceutically acceptable salt thereof, and a pharmaceutically acceptable auxiliary substance, in particular an inert carrier.

E37 A certain embodiment of the invention relates to a method for the therapeutic and/or prophylactic treatment of cancer, by administering the compound of P-L-C as described herein, or a pharmaceutically acceptable salt thereof, to a patient.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I or formula P-L-C may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I or formula P-L-C may be prepared in accordance with the schemes described in the examples. The starting material is commercially available or may be prepared in accordance with known methods.

The preparation of compounds of formula I or formula P-L-C is further described in more detail in the schemes below.

amino-imide 1 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Examples of suitable amino-imides 1 include, but are not limited to, 3-aminopiperidine-2,6-dione[60], (3S)-3-aminopiperidine-2,6-dione[61], (3S)-3-aminopiperidine-2,6-dione hydrochloride[62], (3R)-3-aminopiperidine-2,6-dione[63], (3R)-3-aminopiperidine-2,6-dione hydrochloride[64], or 3-(methylamino)piperidine-2,6-dione[65].

Preferred conditions are HATU with N,N-diisopropylethylamine in N,N-dimethylformamide at room temperature for 18 hours.

In cases where a racemic mixture of amino-imide 1 is coupled to an achiral carboxylic acid 2, the coupling reaction affords amide 3 as a racemic mixture which may be separated into its constituent enantiomers using chiral HPLC. In cases where the carboxylic acid 2 contains one or more stereogenic centres, the coupling reaction affords amide 3 as a mixture of diastereomers which may be separated using chiral HPLC.

Scheme 2

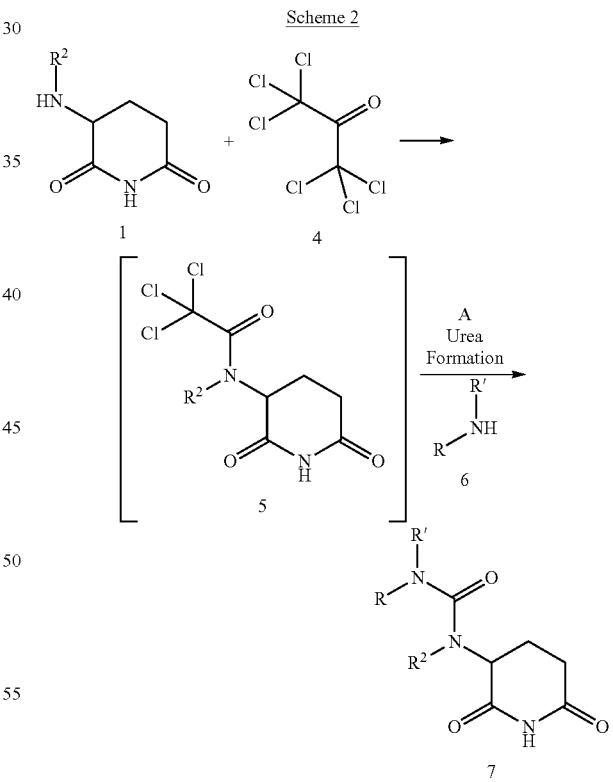

Scheme 1

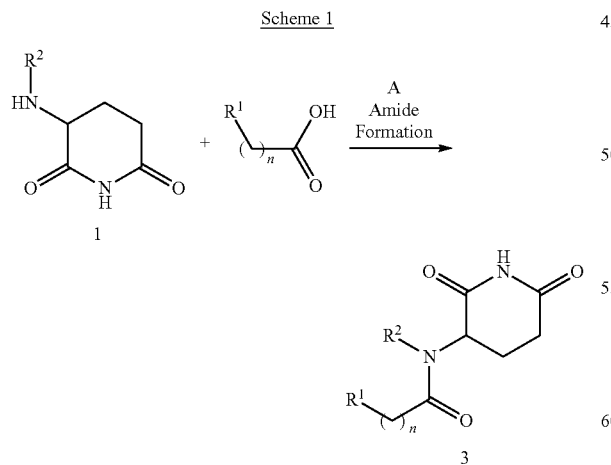

R,R'= H, heterocycloalkyl, heteroaryl or form together with the nitrogen they are attached to a heterocycloalkyl or a heteroaryl
R2 = as described herein The substituents and n are as described herein.
Step A:
Amide bond formation can be accomplished by a coupling reaction between a carboxylic acid 2 and a suitable Step A:
Urea formation can be accomplished by a coupling reaction between a suitable amino-imide 1, triphosgene 4, and a primary or secondary amine 6. The reaction is carried out in a stepwise manner, involving initial reaction of amino-imide 1 and one equivalent of triphosgene 4 to afford intermediate trichloroacetamide 5 which is then reacted in situ with a primary or secondary amine 6 to afford urea 7. The reaction is carried out in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME.

Preferred conditions are triethylamine in 1,2-dichoroethane. The first step to form intermediate 5 is preferably carried out at a temperature between 0° C. and room temperature for 1-2 hours, and the second step to form urea 7 is preferably carried out at room temperature for 18 hours.

Examples of suitable amino-imides 1 include, but are not limited to, 3-aminopiperidine-2,6-dione[60], (3S)-3-aminopiperidine-2,6-dione[61], (3S)-3-aminopiperidine-2,6-dione hydrochloride[62], (3R)-3-aminopiperidine-2,6-dione[63], (3R)-3-aminopiperidine-2,6-dione hydrochloride[64], or 3-(methylamino)piperidine-2,6-dione[65].

In cases where a racemic mixture of amino-imide 1 is coupled to an achiral amine 6, the coupling reaction affords urea 7 as a racemic mixture which may be separated into its constituent enantiomers using chiral HPLC. In cases where the amine 6 contains one or more stereogenic centres, the coupling reaction affords urea 7 as a mixture of diastereomers which may be separated using chiral HPLC.

Scheme 3

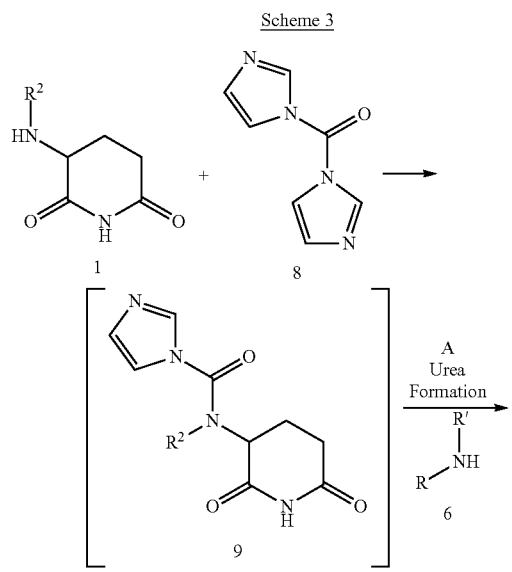

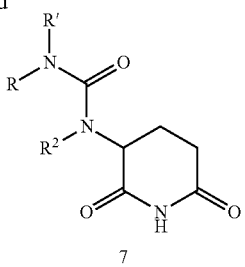

R,R′= H, heterocycloalkyl, heteroaryl or form together with the nitrogen to which they are attached a heterocycloalkyl or a heteroaryl
R2 = as described herein Step A:

Urea formation can also be accomplished by a coupling reaction between a suitable amino-imide 1, 1,1′-carbonyl-di-(1H-imidazole) 4, and a primary or secondary amine 6. The reaction is carried out in a stepwise manner, involving initial reaction of amino-imide 1 and 1,1′-carbonyl-di-(1H-imidazole) 4 to afford intermediate imidazole-1-carboxamide 9 which is then reacted in situ with a primary or secondary amine 6 to afford urea 7. The reaction is carried out in polar aprotic organic solvent such as N-methyl-2-pyrrolidinone or N,N-dimethylformamide, preferably N,N-dimethylformamide. The first step to form intermediate 9 is preferably carried out at room temperature for 1-2 hours, and the second step to form urea 7 is preferably carried out at 80° C. for 3 hours.

Examples of suitable amino-imides 1 include, but are not limited to, 3-aminopiperidine-2,6-dione[60], (3S)-3-aminopiperidine-2,6-dione[61], (3S)-3-aminopiperidine-2,6-dione hydrochloride[62], (3R)-3-aminopiperidine-2,6-dione[63], (3R)-3-aminopiperidine-2,6-dione hydrochloride[64], or 3-(methylamino)piperidine-2,6-dione[65].

In cases where a racemic mixture of amino-imide 1 is coupled to an achiral amine 6, the coupling reaction affords urea 7 as a racemic mixture which may be separated into its constituent enantiomers using chiral HPLC. In cases where the amine 6 contains one or more stereogenic centres, the coupling reaction affords urea 7 as a mixture of diastereomers which may be separated using chiral HPLC.

Scheme 4

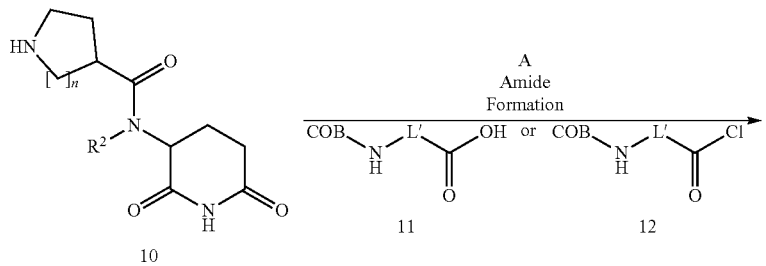

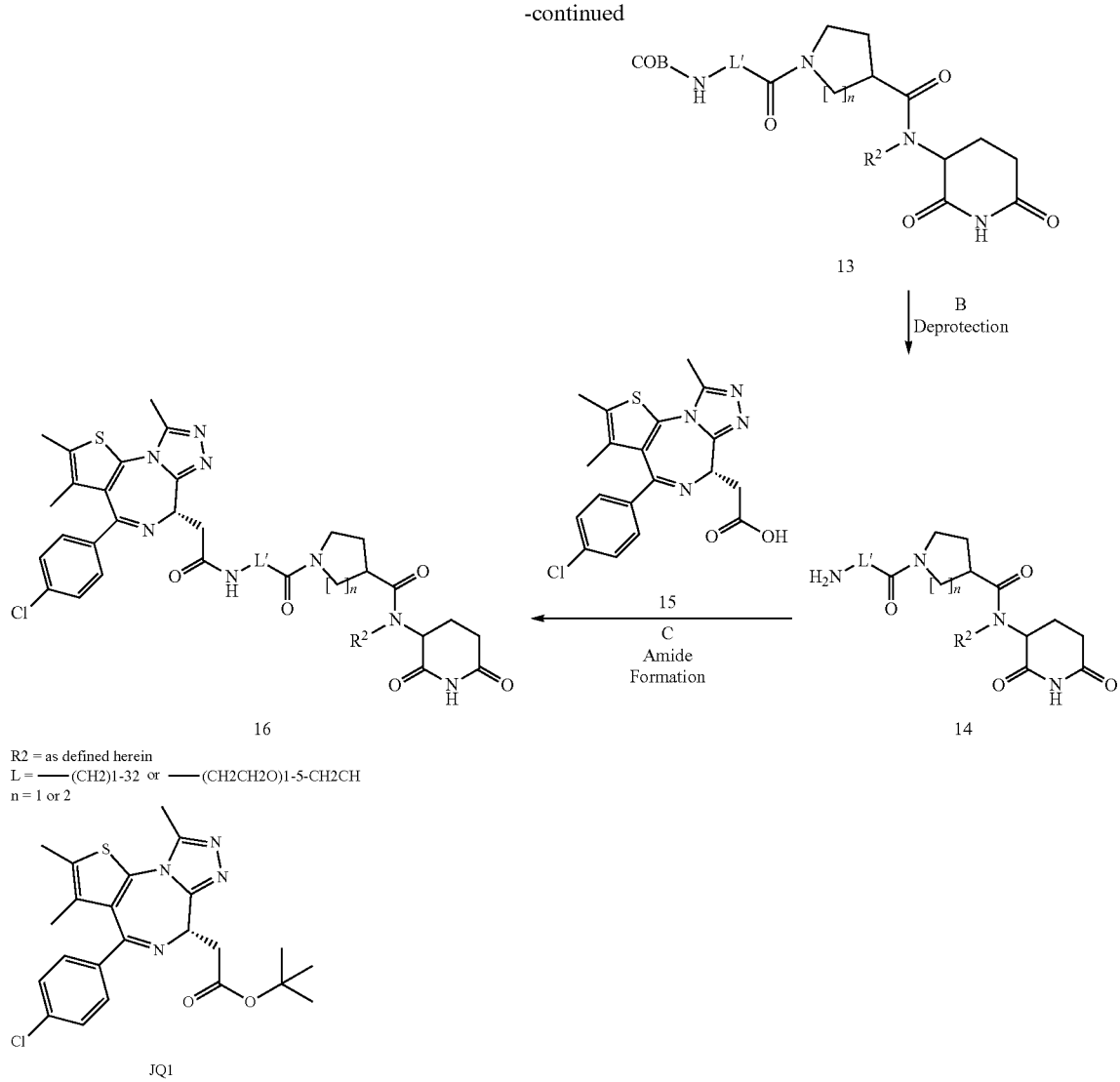

R2 = as defined herein
L = ──(CH2)1-32 or ──(CH2CH2O)1-5-CH2CH
n = 1 or 2

As an illustrative example, degrader compounds targeting the BET bromodomain BRD4 can be prepared based on the known BRD4 ligand JQ1[66] (Filippakopoulos[67]). The synthesis employs the corresponding carboxylic acid derivative 15[68].

Step A:

Amide bond formation can be accomplished by a coupling reaction between amine 10 and a linker-containing compound 11 bearing a terminal carboxylic acid functionality and a terminal BOC-protected amine functionality. The reaction is carried out in the presence of a coupling reagent such as DCC, EDC, TBTU or HATU in the presence of an organic base such as triethylamine, N,N-diisopropylethylamine, N-methylmorpholine or 4-(N,N-dimethylamino)pyridine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Preferred conditions are HATU with N,N-diisopropylethylamine in N,N-dimethylformamide at room temperature for 18 hours.

Alternatively, amide bond formation can be accomplished by a coupling reaction between amine 10 and an acyl chloride compound 12 which has been preformed in situ from a linker-containing compound 11 bearing a terminal carboxylic acid functionality and a terminal BOC-protected amine functionality. The acyl chloride compound 12 can be prepared in situ from the corresponding carboxylic acid 11 by treatment with 1-chloro-N,N,2-trimethylpropenylamine[69] in halogenated solvents such as dichloromethane or 1,2-dichloroethane at a temperature between 0° C. and room temperature, according to the method of Ghosez and co-workers[70]. Amide bond formation can then be accomplished by reaction of the acyl chloride compound 12 with amine 10 in halogenated solvents such as dichloromethane or 1,2-dichloroethane. Preferred conditions are dichoromethane at room temperature for 2 hours.

Step B:

Removal of the Boc N-protecting group of 13 can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, EtOAc, Dioxane, MeOH, EtOH or $H_2O$ at 0 to refluc temperature.

Preferred conditions are 4 M aq. HCl in dioxane and dichoromethane at room temperature for 2 hours.

Step C:

Amide bond formation can be accomplished by a coupling reaction between carboxylic acid 15 and amine 14 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Preferred conditions are HATU with N,N-diisopropylethylamine in N,N-dimethylformamide at room temperature for 2 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compounds of Formula I

In cases where the compounds of formula I are basic they may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Insofar as their preparation is not described in the examples, the compounds of formula I or formula P-L-C as well as all intermediate products can be prepared according to analogous methods or according to the methods set forth herein. Starting materials are commercially available, known in the art or can be prepared by methods known in the art or in analogy thereto.

It will be appreciated that the compounds of general formula I or formula P-L-C in this invention may be derivatised at functional groups to provide derivatives which are capable of conversion back to the parent compound in vivo.

Pharmacological Tests

The compounds of formula I or formula P-L-C and their pharmaceutically acceptable salts possess valuable pharmacological properties. The compounds were investigated in accordance with the test given hereinafter.

Dual Fluorescent Reporter Assay

In order to measure BRD4 protein abundance in a mammalian cell system at medium throughput, a dual fluorescent reporter system was developed based on a principle described in[1]. Transient expression vectors were designed that contain the BRD4 coding sequence (NM_058243.2) fused to a fluorescent tag. Vectors were synthesized at ATUM (Newark, Calif., USA) using the pD2610 CMV backbone and were built up as follows: c-terminal version BRD4_eGFP—IRES—FresnoRFP_NLS, n-terminal version eGFP_BRD4—IRES—FresnoRFP_NLS, empty vector control eGFP—IRES—FresnoRFP_NLS. The c-terminal version was used for the reporter assays, as it presented with the best assay window. HEK293A cells (Invitrogen, Cat. No. R705-07) were cultured in Dulbecco's Modified Eagle Medium (DMEM), 10% fetal calf serum, 2 mM L-Glutamine, 1% Penicillin/Streptomycin. Transfections of the plasmids were performed with Lipofectamine 2000 according to the manufacturer's protocol (Invitrogen, Carlsbad, Calif., USA). 40 hours after transfection, cells were seeded at a density of 40,000/100 ul/96 well flat-bottom and 8 hours later treated with compounds (stocks 10 mM in DMSO) at a 10-point dilution ranging from 0-25 µM. After 16 hours of treatment, cells were washed with PBS, resuspended in Accumax solution (Sigma-Aldrich Cat. No. A7089) and analyzed by flow-cytometry (CytoFlex S, BeckmanCoulter). Single cells were gated based on their forward and side-scatter profiles and pulse-width was used to exclude doublets. A minimum of 20,000 cells was acquired per sample. Analysis was performed with the program Flow Jo V10.1 on BRD4-eGFP low/medium cells ($<10^6$ FL1-A Mean Fluorescence Intensity (MFI)). A factor was derived to normalize BRD4-eGFP values to the RFP protein abundance control (20×FL1A-GFP/FL11A-RFP), then Median and Mode values were calculated and used for comparisons between treatment conditions.

Capillary-Based Immunoassays to Measure Endogenous BRD4 Levels

The biological activity of selected compounds (cut-off >20% reduction in BRD4-eGFP levels) was confirmed in an additional assay which allowed the quantification of endogenous BRD4 levels. To this end, HEK293A cells (origin and culture conditions see above) were seeded at 400,000/300 ul/48 well and were treated 6 hours later with compound concentrations as indicated for. 16 hours after the treatment, the cells were washed with PBS and lysed in 50 ul of UREA lysis buffer (10 mM Tris-HCl pH 8, 2% CHAPS, 7M UREA, 0.4% DTT), supplemented with 1×protease inhibitor cocktail (Complete Mini, Roche) and 1×phosphatase inhibitor cocktail (PhosSTOP, Sigma-Aldrich). Samples were then analyzed by Peggy Sue or WES capillary-based immunoassay systems according to the manufacturer's protocol (Protein Simple/Bio-Techne, San Jose, Calif., 95134 USA). Antibodies used were anti-BRD4 (Cell signaling, CST 13440 1:50) and anti-Vinculin (Sigma, V9131, 1:4000). To quantify BRD4 protein levels, the peak signal areas were normalized to the vinculin loading control and to the DMSO condition.

Further, please see Yen et al.[71].

Fluorescence Direct Binding Protocol

Principle

Determination of the affinities of compounds to protein containing one or more tryptophan is measurable by monitoring the fluorescence emission in direct mode. The measurements depending on the protein available amounts are performed either manually in a cuvette on ISS-PC1 photon counting spectrofluorometer or automatically in well plates on a fluorescence plate reader device. Fluorescence titrations are performed at 20° C. in the chosen binding assay buffer by using a defined constant protein concentration against ligand concentration variations. Small aliquots of known ligand concentration solubilized in DMSO were added and the fluorescence, excited at 280 nm, was recorded at 340 nm. The fluorescence intensity was corrected for protein dilution and for the filter effect (Birdsall et al.[72]). The corrected fluorescence intensity was plotted against the ligand concentration and fitted using a four-parameter sigmoidal function, from which the equilibrium dissociation constant Kd was computed using the law of mass action assuming a 1:1 protein-ligand complex (Eftink, 1997[73]).

Process
1) Optimization of measurement parameters to minimize protein consumption and to minimize the dilution effect and the DMSO content
2) Titration measurements of the protein against ligand by at least 12 titration steps to obtain a good s-curve fit
3) Repeat the same titration measurements with the ligand alone to enable correction
4) Check the stability of the protein once by titration against DMSO alone
5) Determination of the molar extinction coefficients of the ligand at 280 and 340 nm with help of an UV-spectrophotometer
6) Use Excel template for the correction of the measured raw data
7) Use GraphPad Prism software for the quadratic binding fit and the $K_D$ evaluation.

Experimental Details

TABLE 1

Protein - buffers, Reference compound: thalidomide, Contergan, Softenon

| | |
|---|---|
| Protein Batch # | Cereblon_17_13 |
| Construct name | hCereblon(M1-L442)_hDDB1(M1-H1140) |
| Concentration | 2.54 mg/ml |
| MW | 180180 Da |
| Molar extinction coefficient | $\varepsilon_{280} = 165045$ $M^{-1}.cm^{-1}$ |
| Storage buffer | 20 mM MES pH 6.5 200 mM NaCl 1 mM TCEP |
| Assay buffer | 50 mM Hepes 7.4 200 mM NaCl |

TABLE 2

Settings

| | |
|---|---|
| Device | ISS-PC1 |
| Excitation wavelength [nm] | 280 |
| Emission wavelength [nm] | 340 |
| Cuvette | Hellma 115F-QS |
| Volume [µL] | 500 |

Protein preparation:

TABLE 3

Protein preparation

| Volume Protein [µL] | Volume buffer [µL] | Protein concentration [M] |
|---|---|---|
| 1.8 @ 2.54 mg/ml | 498.2 | 50E-8 |

TABLE 4

Titration steps

| C Lig [M] | C Aliquot [M] | V Aliquot [µL] | C Prot [M] | Dilution factor |
|---|---|---|---|---|
| 1E-10 | 1.0E-07 | 0.5 | 4.995E-08 | 1.001 |
| 1.1E-09 | 1.0E-06 | 0.5 | 4.990E-08 | 1.002 |
| 3.1E-09 | 1.0E-06 | 1 | 4.980E-08 | 1.004 |
| 5.1E-09 | 1.0E-06 | 1 | 4.970E-08 | 1.006 |
| 1.51E-08 | 1.0E-05 | 0.5 | 4.965E-08 | 1.007 |
| 2.51E-08 | 1.0E-05 | 0.5 | 4.960E-08 | 1.008 |
| 4.51E-08 | 1.0E-05 | 1 | 4.950E-08 | 1.01 |
| 6.51E-08 | 1.0E-05 | 1 | 4.941E-08 | 1.012 |
| 1.651E-07 | 1.0E-04 | 0.5 | 4.936E-08 | 1.013 |
| 3.651E-07 | 1.0E-04 | 1 | 4.926E-08 | 1.015 |
| 5.651E-07 | 1.0E-04 | 1 | 4.916E-08 | 1.017 |
| 7.651E-07 | 1.0E-04 | 1 | 4.907E-08 | 1.019 |
| 9.651E-07 | 1.0E-04 | 1 | 4.897E-08 | 1.021 |
| 1.9651E-06 | 1.0E-03 | 0.5 | 4.892E-08 | 1.022 |
| 2.9651E-06 | 1.0E-03 | 0.5 | 4.888E-08 | 1.023 |
| 1.29651E-05 | 1.0E-02 | 0.5 | 4.883E-08 | 1.024 |
| 2.29651E-05 | 1.0E-02 | 0.5 | 4.878E-08 | 1.025 |
| 4.29651E-05 | 1.0E-02 | 1 | 4.869E-08 | 1.027 |
| 6.29651E-05 | 1.0E-02 | 1 | 4.859E-08 | 1.029 |
| 8.29651E-05 | 1.0E-02 | 1 | 4.850E-08 | 1.031 |

TABLE 5 affinities of examples to protein

| Example | Name | Fluorescence h-Cereblon_DDB1 Mean $K_d\_EQ$ (µm) |
|---|---|---|
| 1 | N-[(3S)-2,6-dioxo-3-piperidyl]-2-phenyl-acetamide | 0.027 |
| 2 | N-(2,6-dioxo-3-piperidyl)indane-1-carboxamide | 0.655 |
| 3 | N-(2,6-dioxo-3-piperidyl)-2-propyl-isoindoline-1-carboxamide | 0.057 |
| 4 | N-(2,6-dioxo-3-piperidyl)indane-1-carboxamide, isomer A | 0.068 |
| 5 | N-(2,6-dioxo-3-piperidyl)indane-1-carboxamide, isomer B | 0.197 |
| 6 | N-(2,6-dioxo-3-piperidyl)indane-1-carboxamide | 0.146 |
| 7 | N-(2,6-dioxo-3-piperidyl)-1H-indole-3-carboxamide | 0.028 |
| 8 | N-(2,6-dioxo-3-piperidyl)-1-methyl-indole-3-carboxamide | 0.030 |
| 9 | N-(2,6-dioxo-3-piperidyl)indoline-1-carboxamide | 0.002 |
| 10 | N-(2,6-dioxo-3-piperidyl)benzamide | 0.020 |
| 11 | N-(2,6-dioxo-3-piperidyl)cyclopentanecarboxamide | 0.012 |
| 12 | N-(2,6-dioxo-3-piperidyl)benzofuran-3-carboxamide | 0.002 |
| 13 | N-(2,6-dioxo-3-piperidyl)benzothiophene-3-carboxamide | 0.008 |
| 14 | (1R)-N-(2,6-dioxo-3-piperidyl)tetralin-1-carboxamide | 0.004 |
| 15 | (1S)-N-(2,6-dioxo-3-piperidyl)tetralin-1-carboxamide | <0.001 |
| 16 | N-(2,6-dioxo-3-piperidyl)-N-methyl-1H-indole-3- | 0.003 |

TABLE 5-continued affinities of examples to protein

| Example | Name | Fluorescence h-Cereblon_DDB1 Mean $K_d$_EQ (μm) |
|---|---|---|
| | carboxamide | |
| 17 | N-[(3S)-2,6-dioxo-3-piperidyl]-1H-indole-3-carboxamide | 0.014 |
| 18 | N-[(3R)-2,6-dioxo-3-piperidyl]-1H-indole-3-carboxamide | 0.014 |
| 19 | N-((S)-2,6-dioxopiperidin-3-yl)-6,7-dihydro-5H-cyclopenta[b]pyridine-5-carboxamide | 0.001 |
| 20 | N-((R)-2,6-dioxopiperidin-3-yl)-6,7-dihydro-5H-cyclopenta[b]pyridine-5-carboxamide | 0.003 |
| 21 | (S)-N-(2,6-dioxopiperidin-3-yl)benzofuran-3-carboxamide | 0.001 |
| 22 | (N-((R)-2,6-dioxopiperidin-3-yl)-6,7-dihydro-5H-cyclopenta[b]pyridine-7-carboxamide | <0.001 |
| 23 | N-((S)-2,6-dioxopiperidin-3-yl)-6,7-dihydro-5H-cyclopenta[b]pyridine-7-carboxamide | 0.025 |
| 24 | (R)-N-(2,6-dioxopiperidin-3-yl)benzo[b]thiophene-3-carboxamide | 0.009 |
| 25 | (S)-N-(2,6-dioxopiperidin-3-yl)benzo[b]thiophene-3-carboxamide | 0.023 |
| 26 | (S)-N-((R)-2,6-dioxopiperidin-3-yl)-1,2,3,4-tetrahydronaphthalene-1-carboxamide | 0.006 |
| 27 | (S)-N-((S)-2,6-dioxopiperidin-3-yl)-1,2,3,4-tetrahydronaphthalene-1-carboxamide | 0.003 |
| 28 | (S)-N-(2,6-dioxopiperidin-3-yl)-3,4-dihydroquinoline-1(2H)-carboxamide | 0.004 |
| 29 | (S)-N-(2,6-dioxopiperidin-3-yl)-2,3-dihydro-1H-pyrrolo[2,3-b]pyridine-1-carboxamide | <0.001 |
| 30 | (S)-N-(2,6-dioxopiperidin-3-yl)-3,4-dihydro-1,8-naphthyridine-1(2H)-carboxamide | 0.004 |
| 31 | N-[(3S)-2,6-dioxo-3-piperidyl]chromane-4-carboxamide | 0.005 |
| 32 | (4S)-N-[(3S)-2,6-dioxopiperidin-3-yl]-1,2,3,4-tetrahydroquinoline-4-carboxamide | <0.001 |
| 33 | (4R)-N-[(3S)-2,6-dioxopiperidin-3-yl]-1,2,3,4-tetrahydroquinoline-4-carboxamide | 0.006 |
| 34 | (R)-N-(2,6-dioxopiperidin-3-yl)benzofuran-3-carboxamide | 0.026 |
| 35 | (R)-N-(2,6-dioxopiperidin-3-yl)-3,4-dihydroquinoline-1(2H)-carboxamide | 0.019 |
| 36 | (R)-N-(2,6-dioxopiperidin-3-yl)-2,3-dihydro-1H-pyrrolo[2,3-b]pyridine-1-carboxamide | 0.010 |
| 37 | N-[(3S)-2,6-dioxo-3-piperidyl]-1,2,3,4-tetrahydroquinoline-4-carboxamide | <0.001 |
| 38 | N-[(3S)-2,6-dioxo-3-piperidyl]-1-methyl-3,4-dihydro-2H-quinoline-4-carboxamide | 0.005 |
| 39 | N-[(3R)-2,6-dioxo-3-piperidyl]-1,2,3,4-tetrahydroquinoline-4-carboxamide | 0.019 |
| 40 | N-[(3R)-2,6-dioxo-3-piperidyl]-1-methyl-3,4-dihydro-2H-quinoline-4-carboxamide | 0.068 |
| 41 | N-[(3R)-2,6-dioxo-3-piperidyl]chromane-4-carboxamide | 0.014 |
| 42 | methyl (S)-3-((2,6-dioxopiperidin-3-yl)carbamoyl)-1H-indole-6-carboxylate | 0.018 |
| 43 | (4S)-N-((3R)-2,6-dioxopiperidin-3-yl)-1,2,3,4-tetrahydroquinoline-4-carboxamide | <0.001 |
| 44 | (4R)-N-[(3R)-2,6-dioxopiperidin-3-yl]-1,2,3,4-tetrahydroquinoline-4-carboxamide | 0.012 |
| 45 | (1R)-N-((3R)-2,6-dioxopiperidin-3-yl)-1,2,3,4-tetrahydronaphthalene-1-carboxamide | 0.004 |
| 46 | (1R)-N-((3S)-2,6-dioxopiperidin-3-yl)-1,2,3,4-tetrahydronaphthalene-1-carboxamide | 0.039 |
| 47 | (S)-N-(2,6-dioxopiperidin-3-yl)pyrazolo[1,5-a]pyridine-3-carboxamide | <0.001 |
| 48 | (R)-N-(2,6-dioxopiperidin-3-yl)pyrazolo[1,5-a]pyridine-3-carboxamide | <0.001 |
| 49 | (R)-N-(2,6-dioxopiperidin-3-yl)-1H-indazole-3-carboxamide | <0.001 |
| 50 | (S)-N-(2,6-dioxopiperidin-3-yl)imidazo[1,5-a]pyridine-3-carboxamide | 0.004 |
| 51 | (R)-N-(2,6-dioxopiperidin-3-yl)imidazo[1,5-a]pyridine-3-carboxamide | 0.003 |
| 52 | (S)-N-(2,6-dioxopiperidin-3-yl)indolizine-3-carboxamide | 0.006 |
| 53 | (R)-N-(2,6-dioxopiperidin-3-yl)indolizine-3-carboxamide | 0.002 |
| 54 | (S)-N-(2,6-dioxopiperidin-3-yl)imidazo[1,2-a]pyridine-3-carboxamide | 0.001 |
| 55 | (R)-N-(2,6-dioxopiperidin-3-yl)imidazo[1,2-a]pyridine-3-carboxamide | <0.001 |
| 56 | (S)-N-(2,6-dioxopiperidin-3-yl)pyrazolo[1,5-a]pyrimidine-3-carboxamide | 0.008 |

TABLE 5-continued affinities of examples to protein

| Example | Name | Fluorescence h-Cereblon_DDB1 Mean $K_d$_EQ (µm) |
|---|---|---|
| 57 | (R)-N-(2,6-dioxopiperidin-3-yl)pyrazolo[1,5-a]pyrimidine-3-carboxamide | 0.007 |
| 58 | N-(2,6-dioxopiperidin-3-yl)-N-methylindoline-1-carboxamide | 0.022 |
| 59 | (S)-N-(2,6-dioxopiperidin-3-yl)-N-methylindoline-1-carboxamide | 0.020 |
| 60 | (R)-N-(2,6-dioxopiperidin-3-yl)-N-methylindoline-1-carboxamide | 0.030 |
| 61 | (S)-N-(2,6-dioxopiperidin-3-yl)-2-(pyridin-3-yl)acetamide | 0.967 |
| 62 | N-(2,6-dioxopiperidin-3-yl)-N-methyl-2,3-dihydro-1H-pyrrolo[2,3-b]pyridine-1-carboxamide | 0.029 |
| 63 | (R)-N-(2,6-dioxopiperidin-3-yl)-2-(pyridin-3-yl)acetamide | 0.019 |
| 64 | (R)-N-(2,6-dioxopiperidin-3-yl)-3,4-dihydro-1,8-naphthyridine-1(2H)-carboxamide | 0.641 |
| 65 | (S)-2-(4-acetamidophenyl)-N-(2,6-dioxopiperidin-3-yl)acetamide | 0.023 |
| 66 | (R)-2-(4-acetamidophenyl)-N-(2,6-dioxopiperidin-3-yl)acetamide | 0.086 |
| 67 | (R)-2-(3-acetamidophenyl)-N-(2,6-dioxopiperidin-3-yl)acetamide | 0.003 |
| 68 | (S)-2-(3-acetamidophenyl)-N-(2,6-dioxopiperidin-3-yl)acetamide | 0.060 |
| 69 | (S)-N-(2,6-dioxopiperidin-3-yl)-2-(2-oxoindolin-5-yl)acetamide | 0.015 |
| 70 | (R)-N-(2,6-dioxopiperidin-3-yl)-2-(2-oxoindolin-5-yl)acetamide | 0.003 |
| 71 | tert-butyl (S)-3-((2,6-dioxopiperidin-3-yl)carbamoyl)-1-methyl-1,4,6,7-tetrahydro-5H-pyrazolo[4,3-c]pyridine-5-carboxylate | 0.004 |
| 72 | (S)-N-(2,6-dioxopiperidin-3-yl)-1-methyl-4,5,6,7-tetrahydro-1H-pyrazolo[4,3-c]pyridine-3-carboxamide | 0.194 |
| 73 | (1S)-N-(1-methyl-2,6-dioxopiperidin-3-yl)-1,2,3,4-tetrahydronaphthalene-1-carboxamide | 0.028 |
| 74 | (1S)-N-(1-methyl-2,6-dioxopiperidin-3-yl)-1,2,3,4-tetrahydronaphthalene-1-carboxamide, isomer A | 0.005 |
| 75 | (1S)-N-(1-methyl-2,6-dioxopiperidin-3-yl)-1,2,3,4-tetrahydronaphthalene-1-carboxamide, isomer B | 0.046 |
| A | (4S)-1-[6-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]hexanoyl]-N-[(3S)-2,6-dioxo-3-piperidyl]-3,4-dihydro-2H-quinoline-4-carboxamide | 0.010 |
| B | (4S)-1-[6-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]hexanoyl]-N-[(3R)-2,6-dioxo-3-piperidyl]-3,4-dihydro-2H-quinoline-4-carboxamide | 0.037 |
| C | (4R)-1-[2-[2-[2-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]ethoxy]ethoxy]ethoxy]acetyl]-N-[(3S)-2,6-dioxo-3-piperidyl]-3,4-dihydro-2H-quinoline-4-carboxamide | 0.008 |

Pharmaceutical Compositions

The compounds of formula I or formula P-L-C and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I or formula P-L-C and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or formula P-L-C or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I or formula P-L-C. Examples of compositions according to the invention are:

Example A

Tablets of the following composition are manufactured in the usual manner:

TABLE 6 possible tablet composition

| ingredient | mg/tablet | | | |
|---|---|---|---|---|
| | 5 | 25 | 100 | 500 |
| Compound of formula I or formula P-L-C | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 7 possible capsule ingredient composition

| ingredient | mg/capsule | | | |
|---|---|---|---|---|
| | 5 | 25 | 100 | 500 |
| Compound of formula I or formula P-L-C | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I or formula P-L-C, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 8 possible soft gelatin capsule ingredient composition

| ingredient | mg/capsule |
|---|---|
| Compound of formula I or formula P-L-C | 5 |
| Yellow wax | 8 |
| Hydrogenated Soya bean oil | 8 |
| Partially hydrogenated plant oils | 34 |
| Soya bean oil | 110 |
| Total | 165 |

TABLE 9 possible soft gelatin capsule composition

| ingredient | mg/capsule |
|---|---|
| Gelatin | 75 |
| Glycerol 85 % | 32 |
| Karion 83 | 8 (dry matter) |
| Titan dioxide | 0.4 |
| Iron oxide yellow | 1.1 |
| Total | 116.5 |

Manufacturing Procedure
The compound of formula I or formula P-L-C is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 10 possible suppository composition

| ingredient | mg/supp. |
|---|---|
| Compound of formula I or formula P-L-C | 15 |
| Suppository mass | 1285 |
| Total | 1300 |

Manufacturing Procedure
The suppository mass is melted in a glass or steel vessel, mixed thoroughly and cooled to 45° C. Thereupon, the finely powdered compound of formula I or formula P-L-C is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 11 possible injection solution composition

| ingredient | mg/injection solution. |
|---|---|
| Compound of formula I or formula P-L-C | 3 |
| Polyethylene Glycol 400 | 150 |
| acetic acid | q.s. ad pH 5.0 |
| water for injection solutions | ad 1.0 ml |

Manufacturing Procedure

The compound of formula I or formula P-L-C is dissolved in a mixture of Polyethylene Glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Example E

Sachets of the following composition are manufactured:

TABLE 12 possible sachet composition

| ingredient | mg/sachet |
|---|---|
| Compound of formula I or formula P-L-C | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I or formula P-L-C is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof. Example 1[74]

(S)-N-(2,6-Dioxo-3-piperidinyl)benzeneacetamide

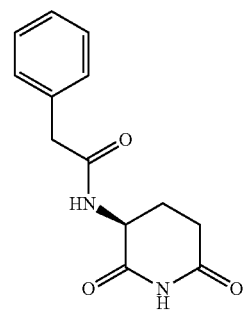 [SMILES: O=C1CC[C@H](NC(=O)Cc2ccccc2)C(=O)N1]

The title compound can be purchased.

Example 2

N-(2,6-Dioxopiperidin-3-yl)-2,3-dihydro-1H-indene-1-carboxamide (RACEMIC MIXTURE OF ALL DIASTEREOMERS)

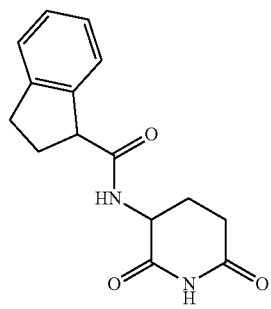 [SMILES: O=C1CCC(NC(=O)C2CCc3ccccc32)C(=O)N1]

To a stirred suspension of 2,3-dihydro-1H-indene-1-carboxylic acid[75] (100 mg), N,N-diisopropylethylamine (323 µl) and 3-aminopiperidine-2,6-dione[60] (86.9 mg) in DMF (1.5 ml) was added HATU (352 mg). The reaction mixture was stirred at room temperature for 18 hours. The resulting yellow solution was directly purified by reversed phase HPLC to afford after lyophilisation N-(2,6-dioxopiperidin-3-yl)-2,3-dihydro-1H-indene-1-carboxamide (RACEMIC MIXTURE OF ALL DIASTEREOMERS) as a white solid (168 mg, 66%). MS (ISP): 273.5 ([M+H]$^+$).

Example 3

N-(2,6-Dioxopiperidin-3-yl)-2-propylisoindoline-1-carboxamide (RACEMIC MIXTURE OF ALL DIASTEREOMERS)

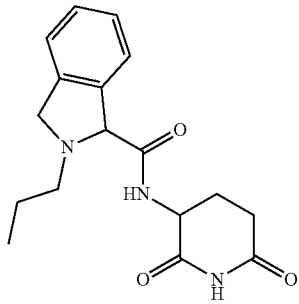 [SMILES: CCCN1Cc2ccccc2C1C(=O)NC1CCC(=O)NC1=O]

a) tert-Butyl 1-((2,6-dioxopiperidin-3-yl)carbamoyl) isoindoline-2-carboxylate The title compound was obtained in analogy to example 2 using (RS)-BOC-1,3-dihydro-2H-isoindole carboxylic acid[76] in place of 2,3-dihydro-1H-indene-1-carboxylic acid[75]. White solid. MS (ISP): 372.4 ([M−H]−).

b) N-(2,6-Dioxopiperidin-3-yl)isoindoline-1-carboxamide Hydrochloride Salt

To a stirred solution of tert-butyl 1-((2,6-dioxopiperidin-3-yl)carbamoyl)isoindoline-2-carboxylate (88 mg) in dichloromethane (2 ml) was added a 4 M solution of HCl in dioxane (884 μl). After stirring for 3 hours, the solvents were evaporated to dryness and diethyl ether was added to the residue. The suspension was sonicated, stirred at 0° C. for 15 min, then filtered to afford N-(2,6-dioxopiperidin-3-yl)isoindoline-1-carboxamide hydrochloride salt as an off-white solid (72 mg, 99%). MS (ISP): 274.1 ([M+H]+).

c) N-(2,6-Dioxopiperidin-3-yl)-2-propylisoindoline-1-carboxamide

To a stirred solution of N-(2,6-dioxopiperidin-3-yl)isoindoline-1-carboxamide hydrochloride salt (63 mg), propionaldehyde[77] (22.2 μl), sodium acetate (16.7 mg) and zinc chloride (111 mg) in MeOH (1.2 ml) was added sodium cyanoborohydride (38.3 mg). The reaction mixture was stirred at room temperature for 5 hours. The reaction mixture was directly purified by reversed phase HPLC to afford N-(2,6-dioxopiperidin-3-yl)-2-propylisoindoline-1-carboxamide as an white solid (31 mg, 48%). MS (ISP): 316.0 ([M+H]+).

Example 4

(−)-N-(2,6-Dioxopiperidin-3-yl)-2,3-dihydro-1H-indene-1-carboxamide (EPIMER 1)

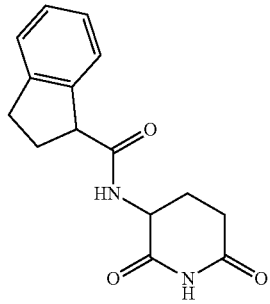 [SMILES: O=C1CCC(NC(=O)C2CCc3ccccc32)C(=O)N1]

The diastereomers of N-(2,6-dioxopiperidin-3-yl)-2,3-dihydro-1H-indene-1-carboxamide from example 2 (95 mg) were separated using chiral HPLC (column: Reprosil Chiral-NR, eluent: heptane/ethanol+NH4OAc (70:30), pressure: 18 bar; flow rate: 35 ml/min) to afford (−)-N-(2,6-dioxopiperidin-3-yl)-2,3-dihydro-1H-indene-1-carboxamide (EPIMER 1) (17 mg, white solid), retention time=36.1 min. MS (ISP): 273.1 ([M+H]+).

Example 5

(+)-N-(2,6-Dioxopiperidin-3-yl)-2,3-dihydro-1H-indene-1-carboxamide (EPIMER 2)

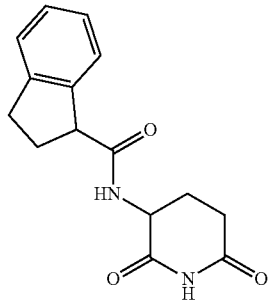 [SMILES: O=C1CCC(NC(=O)C2CCc3ccccc32)C(=O)N1]

The diastereomers of N-(2,6-dioxopiperidin-3-yl)-2,3-dihydro-1H-indene-1-carboxamide from example 2 (95 mg) were separated using chiral HPLC (column: Reprosil Chiral-NR, eluent: heptane/ethanol+NH4OAc (70:30), pressure: 18 bar; flow rate: 35 ml/min) to afford (+)-N-(2,6-dioxopiperidin-3-yl)-2,3-dihydro-1H-indene-1-carboxamide (EPIMER 2) (15 mg, white solid), retention time=45 min. MS (ISP): 273.1 ([M+H]+).

Example 6

N-(2,6-Dioxopiperidin-3-yl)-2,3-dihydro-1H-indene-1-carboxamide (EPIMERS 3 & 4)

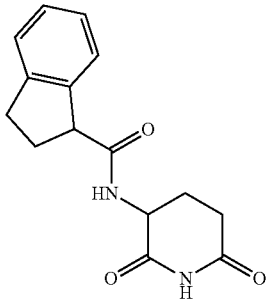

The diastereomers of N-(2,6-dioxopiperidin-3-yl)-2,3-dihydro-1H-indene-1-carboxamide from example 2 (95 mg) were separated using chiral HPLC (column: Reprosil Chiral-NR, eluent: heptane/ethanol+NH$_4$OAc (70:30), pressure: 18 bar; flow rate: 35 ml/min) to afford a mixture of two epimers of N-(2,6-dioxopiperidin-3-yl)-2,3-dihydro-1H-indene-1-carboxamide (EPIMER 3 & 4) (28 mg, white solid), retention time=63.3 min, MS (ISP): 273.1 ([M+H]$^+$).

Example 7[78]

N-(2,6-Dioxopiperidin-3-yl)-1H-indole-3-carboxamide

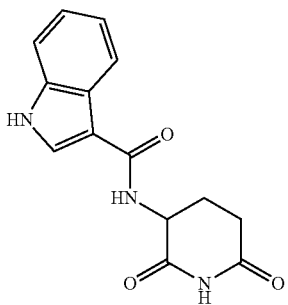 [SMILES: O=C1CCC(NC(=O)c2c[nH]c3ccccc23)C(=O)N1]

The title compound can be purchased.

Example 8[79]

N-(2,6-Dioxopiperidin-3-yl)-1-methyl-1H-indole-3-carboxamide

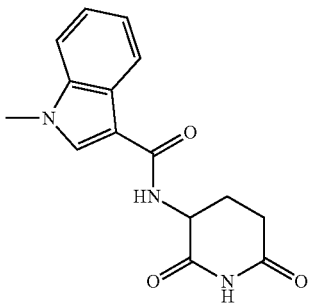 [SMILES: Cn1cc(C(=O)NC2CCC(=O)NC2=O)c2ccccc21]

The title compound can be purchased.

Example 9

N-(2,6-Dioxopiperidin-3-yl)indoline-1-carboxamide

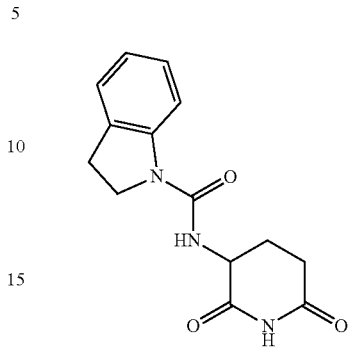

To a stirred suspension of 3-aminopiperidine-2,6-dione[60] (199 mg) and triethylamine (433 µl) in dichloroethane (12 ml) in a sealed tube was added triphosgene (170 mg) at 0-5° C. After stirring at room temperature for 1 hour, indoline[80] (185 mg) was added. The reaction mixture was stirred at room temperature for 18 hours. Some drops of water were added to quench the reaction then the solvent was evaporated to dryness and the residue was purified by reversed phase HPLC (Gemini NX C18, 12 nm, 5µ, 100×30 mm, 40 ml/min, CH$_3$CN/H$_2$O+formic acid) to afford, after lyophilisation, N-(2,6-dioxopiperidin-3-yl)indoline-1-carboxamide as a yellow solid (24 mg, 6%). MS (ISP): 274.2 ([M+H]$^+$).

Example 10[81]

N-(2,6-Dioxopiperidin-3-yl)benzamide

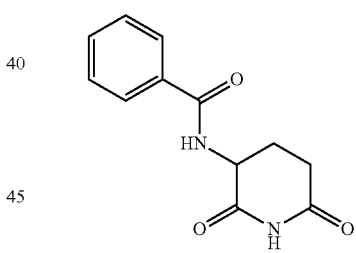

The title compound can be purchased.

Example 11[82]

N-(2,6-Dioxopiperidin-3-yl)cyclopentanecarboxamide

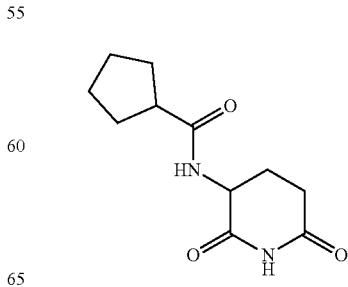

The title compound can be purchased.

Example 12[83]

N-(2,6-Dioxopiperidin-3-yl)benzofuran-3-carboxamide

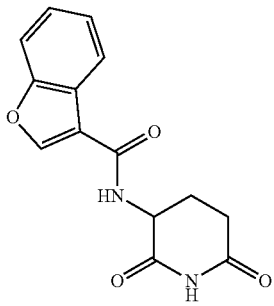

The title compound can be purchased.

Example 13[84]

N-(2,6-Dioxopiperidin-3-yl)benzo[b]thiophene-3-carboxamide

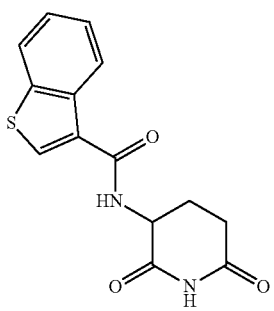 [SMILES: O=C1CCC(NC(=O)c2csc3ccccc23)C(=O)N1]

The title compound can be purchased.

Example 14

(1R)-N-(2,6-Dioxopiperidin-3-yl)-1,2,3,4-tetrahydronaphthalene-1-carboxamide (MIXTURE OF 2 EPIMERS)

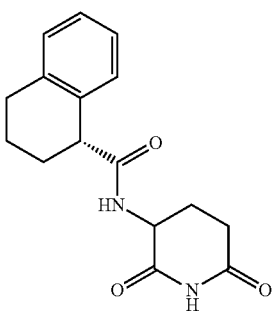 [SMILES: O=C1CCC(NC(=O)[C@@H]2CCCc3ccccc32)C(=O)N1]

The title compound was obtained in analogy to example 2 using (R)-1,2,3,4-tetrahydronaphthoic acid[85] in place of 2,3-dihydro-1H-indene-1-carboxylic acid[75]. White solid. MS (ISP): 287 ([M+H]$^+$).

Example 15

(1S)-N-(2,6-Dioxopiperidin-3-yl)-1,2,3,4-tetrahydronaphthalene-1-carboxamide (MIXTURE OF 2 EPIMERS)

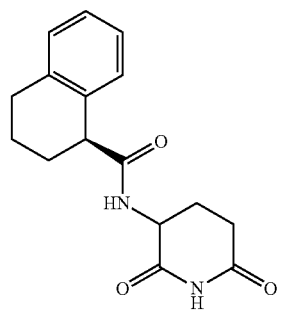 [SMILES: O=C1CCC(NC(=O)[C@H]2CCCc3ccccc32)C(=O)N1]

The title compound was obtained in analogy to example 2 using (S)-1,2,3,4-tetrahydronaphthoic acid[86] in place of 2,3-dihydro-1H-indene-1-carboxylic acid[75]. White solid. MS (ISP): 287 ([M+H]$^+$).

Example 16

N-(2,6-Dioxopiperidin-3-yl)-N-methyl-1H-indole-3-carboxamide

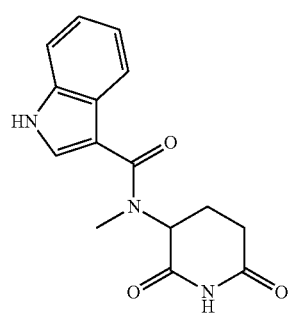 [SMILES: CN(C(=O)c1c[nH]c2ccccc12)C1CCC(=O)NC1=O]

The title compound was obtained in analogy to example 2 using 1H-indole-3-carboxylic acid[87] in place of 2,3-dihydro-1H-indene-1-carboxylic acid[75] and 3-(methylamino)piperidine-2,6-dione[65] in place of 3-aminopiperidine-2,6-dione[60]. Light blue solid. MS (ISP): 286.2 ([M+H]$^+$).

Example 17

(S)-N-(2,6-Dioxopiperidin-3-yl)-1H-indole-3-carboxamide

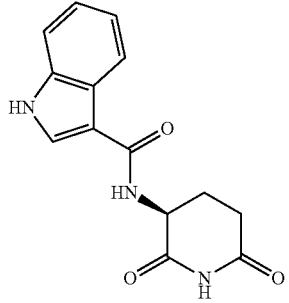 [SMILES: O=C1CC[C@H](NC(=O)c2c[nH]c3ccccc23)C(=O)N1]

The title compound was obtained in analogy to example 2 using 1H-indole-3-carboxylic acid[87] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 272.2 ([M+H]+).

Example 18

(R)-N-(2,6-Dioxopiperidin-3-yl)-1H-indole-3-carboxamide

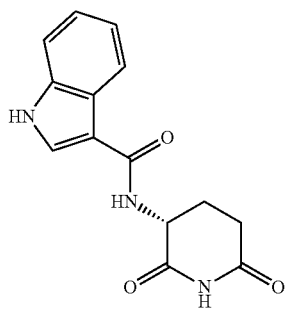 [SMILES: O=C1CC[C@@H](NC(=O)c2c[nH]c3ccccc23)C(=O)N1]

The title compound was obtained in analogy to example 2 using 1H-indole-3-carboxylic acid[87] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP):272.2 ([M+H]+).

Example 19

N-((S)-2,6-Dioxopiperidin-3-yl)-6,7-dihydro-5H-cyclopenta[b]pyridine-5-carboxamide (MIXTURE OF 2 EPIMERS)

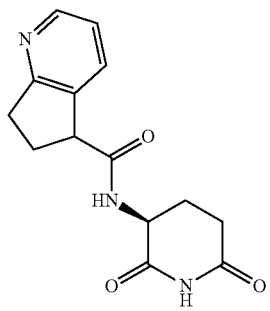 [SMILES: O=C1CC[C@H](NC(=O)C2CCc3ncccc32)C(=O)N1]

The title compound was obtained in analogy to example 2 using (RS)-6,7-dihydro-5H-cyclopenta[b]pyridine-5-carboxylic acid[88] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 274.3 ([M+H]+).

Example 20

N-((R)-2,6-Dioxopiperidin-3-yl)-6,7-dihydro-5H-cyclopenta[b]pyridine-5-carboxamide (MIXTURE OF 2 EPIMERS)

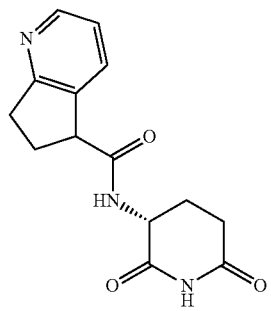 [SMILES: O=C1CC[C@@H](NC(=O)C2CCc3ncccc32)C(=O)N1]

The title compound was obtained in analogy to example 2 using (RS)-6,7-dihydro-5H-cyclopenta[b]pyridine-5-carboxylic acid[88] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 274.3 ([M+H]+).

Example 21

(S)-N-(2,6-Dioxopiperidin-3-yl)benzofuran-3-carboxamide

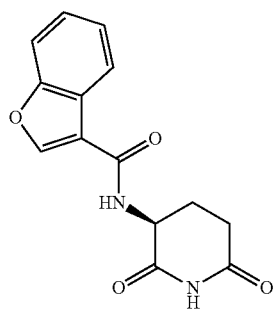 [SMILES: O=C1CC[C@H](NC(=O)c2coc3ccccc23)C(=O)N1]

The title compound was obtained in analogy to example 2 using benzofuran-3-carboxylic acid in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 273.2 ([M+H]+).

Example 22

(N-((R)-2,6-Dioxopiperidin-3-yl)-6,7-dihydro-5H-cyclopenta[b]pyridine-7-carboxamide (MIXTURE OF 2 EPIMERS)

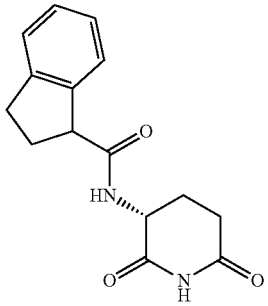 [SMILES: O=C1CC[C@@H](NC(=O)C2CCc3ccccc32)C(=O)N1]

The title compound was obtained in analogy to example 2 using (3R)-3-aminopiperidine-2,6-dione hydrochloride[64] in place of 3-aminopiperidine-2,6-dione[60]. White solid. MS (ISP): 274.2 ([M+H]$^+$).

Example 23

N-((S)-2,6-Dioxopiperidin-3-yl)-6,7-dihydro-5H-cyclopenta[b]pyridine-7-carboxamide (MIXTURE OF 2 EPIMERS)

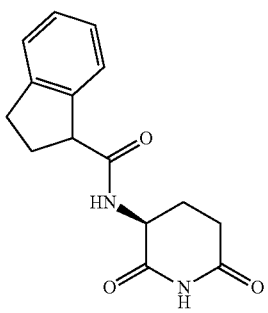 [SMILES: O=C1CC[C@H](NC(=O)C2CCc3ccccc32)C(=O)N1]

The title compound was obtained in analogy to example 2 using (3S)-3-aminopiperidine-2,6-dione hydrochloride[62] in place of 3-aminopiperidine-2,6-dione[60]. White solid. MS (ISP): 274.2 ([M+H]$^+$).

Example 24

(R)-N-(2,6-Dioxopiperidin-3-yl)benzo[b]thiophene-3-carboxamide

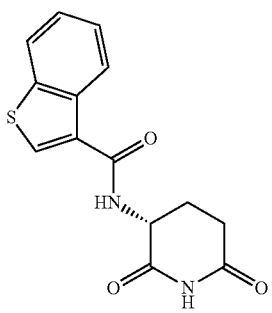 [SMILES: O=C1CC[C@@H](NC(=O)c2csc3ccccc23)C(=O)N1]

The title compound was obtained in analogy to example 2 using benzothiophene-3-carboxylic acid[89] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 289.1 ([M+H]$^+$).

Example 25

(S)-N-(2,6-Dioxopiperidin-3-yl)benzo[b]thiophene-3-carboxamide

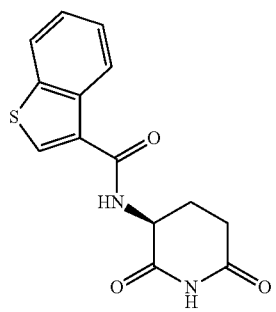 [SMILES: O=C1CC[C@H](NC(=O)c2csc3ccccc23)C(=O)N1]

The title compound was obtained in analogy to example 2 using benzothiophene-3-carboxylic acid[89] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 289.1 ([M+H]$^+$).

Example 26

(S)-N-((R)-2,6-Dioxopiperidin-3-yl)-1,2,3,4-tetrahydronaphthalene-1-carboxamide

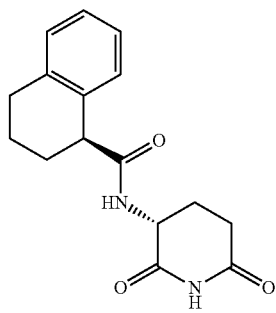

The title compound was obtained in analogy to example 2 using (S)-1,2,3,4-tetrahydronaphthoic acid[86] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 287.1 ([M+H]$^+$).

Example 27

(S)-N-((S)-2,6-Dioxopiperidin-3-yl)-1,2,3,4-tetrahydronaphthalene-1-carboxamide

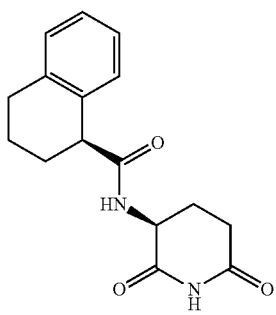 [SMILES: O=C1CC[C@H](NC(=O)[C@H]2CCCc3ccccc32)C(=O)N1]

The title compound was obtained in analogy to example 2 using (S)-1,2,3,4-tetrahydronaphthoic acid in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 287.1 ([M+H]$^+$).

Example 28

(S)-N-(2,6-Dioxopiperidin-3-yl)-3,4-dihydroquinoline-1(2H)-carboxamide

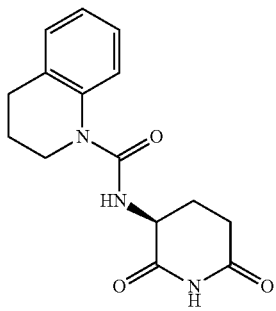 [SMILES: O=C1CC[C@H](NC(=O)N2CCCc3ccccc32)C(=O)N1]

To a stirred suspension of (S)-3-aminopiperidine-2,6-dione hydrochloride[62] (100 mg) in N,N-dimethylformamide (1.5 ml) was added 1,1'-carbonyl-di-(1H-imidazole) (128 mg) and the reaction mixture was stirred for 2 hours at room temperature. 1,2,3,4-Tetrahydroquinoline[90] (125 mg) was added in one portion. The reaction mixture was heated at 80° C. for 3 hours and was then partitioned between ethyl acetate and water. The layers were separated and the aqueous layer was extracted with ethyl acetate (3×25 ml). The combined organic layers were washed with brine, dried over anhydrous sodium sulfate, and concentrated in vacuo. The resulting residue was purified by reversed phase HPLC to afford (S)-N-(2,6-dioxopiperidin-3-yl)-3,4-dihydroquinoline-1 (2H)-carboxamide as a white solid (68 mg, 39%). MS (ISP): 288 ([M+H]$^+$).

Example 29

(S)-N-(2,6-Dioxopiperidin-3-yl)-2,3-dihydro-1H-pyrrolo[2,3-b]pyridine-1-carboxamide

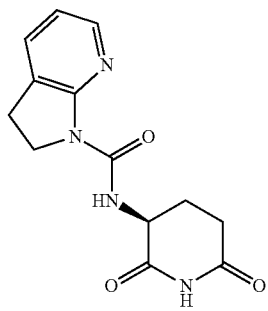 [SMILES: O=C1CC[C@H](NC(=O)N2CCc3cccnc32)C(=O)N1]

The title compound was obtained in analogy to example 28 using 2,3-dihydro-1H-pyrrolo[2,3-b]pyridine[91] in place of 1,2,3,4-tetrahydroquinoline[90]. Yellow solid. MS (ISP): 275 ([M+H]$^+$).

Example 30

(S)-N-(2,6-Dioxopiperidin-3-yl)-3,4-dihydro-1,8-naphthyridine-1 (2H)-carboxamide

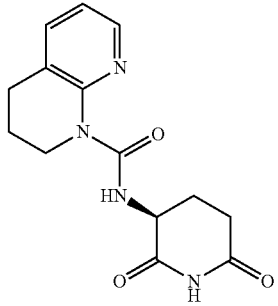 [SMILES: O=C1CC[C@H](NC(=O)N2CCCc3cccnc32)C(=O)N1]

The title compound was obtained in analogy to example 28 using 1,2,3,4-tetrahydro-1,8-naphthyridine[92] in place of 1,2,3,4-tetrahydroquinoline[90]. White solid. MS (ISP): 289.1 ([M+H]$^+$).

Example 31

N-[(3S)-2,6-Dioxo-3-piperidyl]chromane-4-carboxamide (MIXTURE OF 2 EPIMERS)

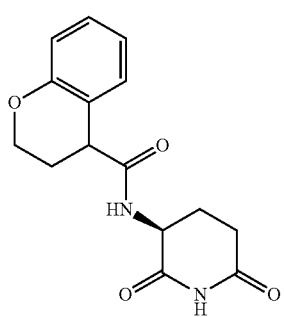 [SMILES: O=C1CC[C@H](NC(=O)C2CCOc3ccccc32)C(=O)N1]

The title compound was obtained in analogy to example 2 using (RS)-chromane-4-carboxylic acid[93] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 289.2 ([M+H]+).

Example 32

(4S)-N-[(3S)-2,6-Dioxopiperidin-3-yl]-1,2,3,4-tetrahydroquinoline-4-carboxamide

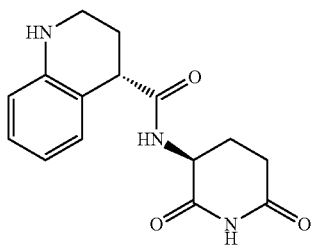 [SMILES: O=C1CC[C@H](NC(=O)[C@H]2CCNc3ccccc32)C(=O)N1]

a) N-((S)-2,6-Dioxopiperidin-3-yl)-1,2,3,4-tetrahydroquinoline-4-carboxamide (MIXTURE OF 2 EPIMERS)

The title compound was obtained in analogy to example 2 using (RS)-1,2,3,4-tetrahydroquinoline-4-carboxylic acid[94] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 288.3 ([M+H]+).

b) (4S)-N-[(3S)-2,6-Dioxopiperidin-3-yl]-1,2,3,4-tetrahydroquinoline-4-carboxamide The epimers of N-((S)-2,6-dioxopiperidin-3-yl)-1,2,3,4-tetrahydroquinoline-4-carboxamide (160 mg) were separated using chiral HPLC (column: Reprosil Chiral-NR, eluent: heptane/ethanol+NH4OAc (60:40), pressure: 18 bar; flow rate: 35 ml/min) affording (4S)-N-[(3S)-2,6-dioxopiperidin-3-yl]-1,2,3,4-tetrahydroquinoline-4-carboxamide (57 mg, white solid), retention time=49 min. MS (ISP): 288.1 ([M+H]+).

Example 33

(4R)-N-[(3S)-2,6-Dioxopiperidin-3-yl]-1,2,3,4-tetrahydroquinoline-4-carboxamide

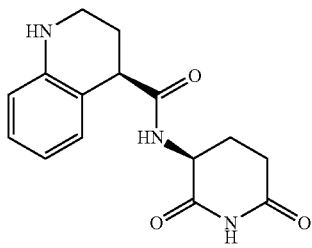 [SMILES: O=C1CC[C@H](NC(=O)[C@@H]2CCNc3ccccc32)C(=O)N1]

The epimers of N-((S)-2,6-dioxopiperidin-3-yl)-1,2,3,4-tetrahydroquinoline-4-carboxamide (160 mg) were separated using chiral HPLC (column: Reprosil Chiral-NR, eluent: heptane/ethanol+NH4OAc (60:40), pressure: 18 bar; flow rate: 35 ml/min) affording (4R)-N-[(3S)-2,6-doxopiperidin-3-yl]-1,2,3,4-tetrahydroquinoline-4-carboxamide (35 mg, white solid), retention time=58 min. MS (ISP): 288.1 ([M+H]+).

Example 34

(R)-N-(2,6-Dioxopiperidin-3-yl)benzofuran-3-carboxamide

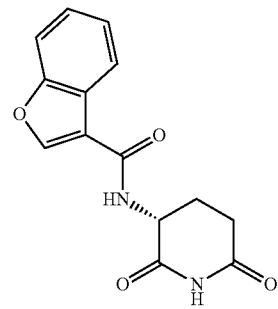 [SMILES: O=C1CC[C@@H](NC(=O)c2coc3ccccc23)C(=O)N1]

The title compound was obtained in analogy to example 2 using benzofuran-3-carboxylic acid[95] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 273.1 ([M+H]+).

Example 35

(R)-N-(2,6-Dioxopiperidin-3-yl)-3,4-dihydroquinoline-1(2H)-carboxamide

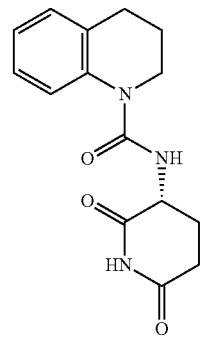 [SMILES: O=C1CC[C@@H](NC(=O)N2CCCc3ccccc32)C(=O)N1]

The title compound was obtained in analogy to example 28 using (R)-3-aminopiperidine-2,6-dione hydrochloride[64] in place of (S)-3-aminopiperidine-2,6-dione hydrochloride[62]. White solid. MS (ISP): 288.1 ([M+H]+).

Example 36

(R)-N-(2,6-Dioxopiperidin-3-yl)-2,3-dihydro-1H-pyrrolo[2,3-b]pyridine-1-carboxamide

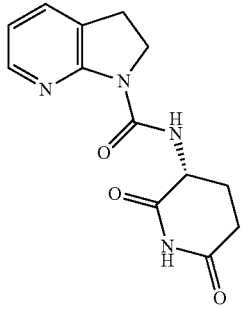 [SMILES: O=C1CC[C@@H](NC(=O)N2CCc3cccnc32)C(=O)N1]

The title compound was obtained in analogy to example 28 using 2,3-dihydro-1H-pyrrolo[2,3-b]pyridine[91] in place of 1,2,3,4-tetrahydroquinoline[90] and (R)-3-aminopiperidine-2,6-dione hydrochloride[64] in place of (S)-3-aminopiperidine-2,6-dione hydrochloride[62]. White solid. MS (ISP): 275.1 ([M+H]$^+$).

Example 37

N-[(3S)-2,6-Dioxo-3-piperidyl]-1,2,3,4-tetrahydroquinoline-4-carboxamide (1:1 MIXTURE OF EPIMERS)

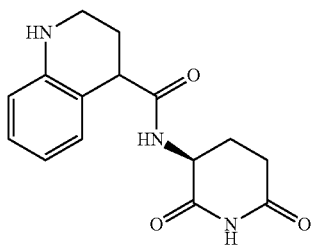 [SMILES: O=C1CC[C@H](NC(=O)C2CCNc3ccccc32)C(=O)N1]

The title compound was obtained in analogy to example 2 using (RS)-1,2,3,4-tetrahydroquinoline-4-carboxylic acid[94] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 288.3 ([M+H]$^+$).

Example 38

N-[(3S)-2,6-Dioxo-3-piperidyl]-1-methyl-3,4-dihydro-2H-quinoline-4-carboxamide (1:1 MIXTURE OF EPIMERS)

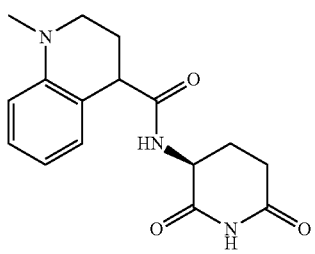 [SMILES: CN1CCC(C(=O)N[C@H]2CCC(=O)NC2=O)c2ccccc21]

The title compound was obtained in analogy to example 2 using (RS)-1-methyl-1,2,3,4-tetrahydroquinoline-4-carboxylic acid[96] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 302.2 ([M+H]$^+$).

Example 39

N-[(3R)-2,6-Dioxo-3-piperidyl]-1,2,3,4-tetrahydroquinoline-4-carboxamide (1:1 MIXTURE OF EPIMERS)

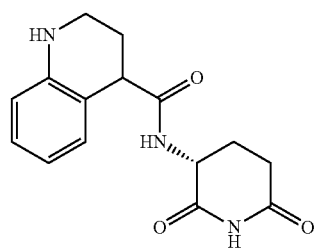 [SMILES: O=C1CC[C@@H](NC(=O)C2CCNc3ccccc32)C(=O)N1]

The title compound was obtained in analogy to example 2 using (RS)-1,2,3,4-tetrahydroquinoline-4-carboxylic acid[94] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 288.3 ([M+H]$^+$).

Example 40

N-[(3R)-2,6-Dioxo-3-piperidyl]-1-methyl-3,4-dihydro-2H-quinoline-4-carboxamide (1:1 MIXTURE OF EPIMERS)

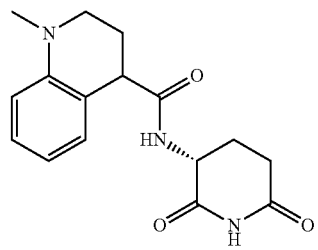 [SMILES: CN1CCC(C(=O)N[C@@H]2CCC(=O)NC2=O)c2ccccc21]

The title compound was obtained in analogy to example 2 using (RS)-1-methyl-1,2,3,4-tetrahydroquinoline-4-carboxylic acid[96] in place of 2,3-dihydro-1H-indene-1-carboxylic acid[75] and (3R)-3-aminopiperidine-2,6-dione hydrochloride[64] in place of 3-aminopiperidine-2,6-dione[60]. Light red solid. MS (ISP): 302.3 ([M+H]$^+$).

Example 41

N-[(3R)-2,6-Dioxo-3-piperidyl]chromane-4-carboxamide (1:1 MIXTURE OF EPIMERS)

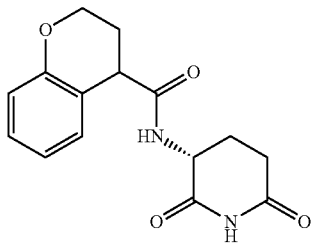 [SMILES: O=C1CC[C@@H](NC(=O)C2CCOc3ccccc32)C(=O)N1]

The title compound was obtained in analogy to example 2 using (RS)-chromane-4-carboxylic acid[97] in place of 2,3-dihydro-1H-indene-1-carboxylic acid[75] and (3R)-3-aminopiperidine-2,6-dione hydrochloride[64] in place of 3-aminopiperidine-2,6-dione[60]. Light red solid. MS (ISP): 289.2 ([M+H]$^+$).

Example 42

Methyl (S)-3-((2,6-dioxopiperidin-3-yl)carbamoyl)-1H-indole-6-carboxylate

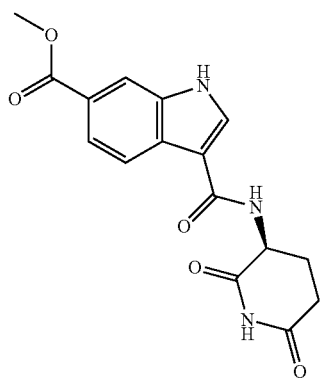 [SMILES: COC(=O)c1ccc2c(C(=O)N[C@H]3CCC(=O)NC3=O)c[nH]c2c1]

The title compound was obtained in analogy to example 2 using 6-methoxycarbonyl-1H-indole-3-carboxylic acid[98] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 330.1 ([M+H]$^+$).

Example 43

(4S)-N-[(3R)-2,6-Dioxopiperidin-3-yl]-1,2,3,4-tetrahydroquinoline-4-carboxamide

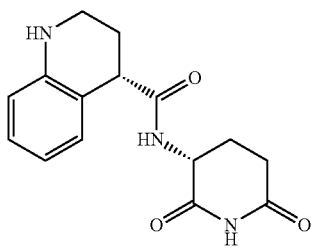 [SMILES: O=C1CC[C@@H](NC(=O)[C@H]2CCNc3ccccc32)C(=O)N1]

a) N-[(3R)-2,6-dioxo-3-piperidyl]-1,2,3,4-tetrahydroquinoline-4-carboxamide (MIXTURE OF 2 EPIMERS)

The title compound was obtained in analogy to example 2 using (RS)-1,2,3,4-tetrahydroquinoline-4-carboxylic acid[94] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 288.3 ([M+H]$^+$).

b) (4S)-N-[(3R)-2,6-Dioxopiperidin-3-yl]-1,2,3,4-tetrahydroquinoline-4-carboxamide The epimers of N-[(3R)-2,6-dioxopiperidin-3-yl]-1,2,3,4-tetrahydroquinoline-4-carboxamide (110 mg) from step a were separated using chiral HPLC (column: Reprosil Chiral-NR, eluent: heptane/ethanol+NH$_4$OAc (60:40), pressure: 18 bar; flow rate: 35 ml/min) to afford (4S)-N-[(3R)-2,6-dioxopiperidin-3-yl]-1,2,3,4-tetrahydroquinoline-4-carboxamide (32 mg, white solid), retention time=39 min. MS (ISP): 288.1 ([M+H]$^+$).

Example 44

(4R)-N-[(3R)-2,6-Dioxopiperidin-3-yl]-1,2,3,4-tetrahydroquinoline-4-carboxamide

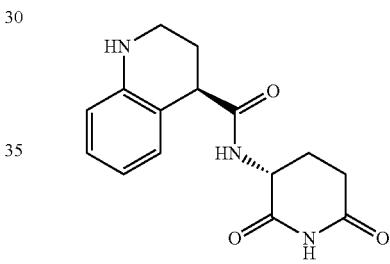

The epimers of N-[(3R)-2,6-dioxopiperidin-3-yl]-1,2,3,4-tetrahydroquinoline-4-carboxamide (110 mg) were separated using chiral HPLC (column: Reprosil Chiral-NR, eluent: heptane/ethanol+NH$_4$OAc (60:40), pressure: 18 bar; flow rate: 35 ml/min) to afford (4R)-N-[(3R)-2,6-dioxopiperidin-3-yl]-1,2,3,4-tetrahydroquinoline-4-carboxamide (37 mg, white solid), retention time=53 min. MS (ISP): 288.1 ([M+H]$^+$).

Example 45

(1R)-N-[(3R)-2,6-Dioxopiperidin-3-yl]-1,2,3,4-tetrahydronaphthalene-1-carboxamide

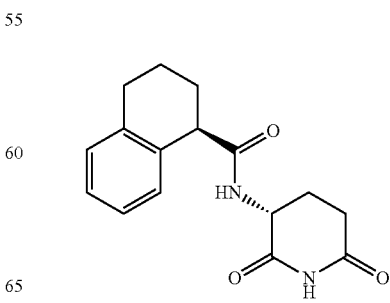

a) N-[(3R)-2,6-Dioxopiperidin-3-yl]-1,2,3,4-tetrahydronaphthalene-1-carboxamide (MIXTURE OF 2 EPIMERS)

The title compound was obtained in analogy to example 2 using (RS)-1,2,3,4-tetrahydronaphthalene-1-carboxylic acid[99] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 287.1 ([M+H]$^+$).

b) (1R)-N-[(3R)-2,6-Dioxopiperidin-3-yl]-1,2,3,4-tetrahydronaphthalene-1-carboxamide The epimers of N-[(3R)-2,6-dioxopiperidin-3-yl]-1,2,3,4-tetrahydronaphthalene-1-carboxamide (250 mg) from step a were separated using chiral HPLC (column: Reprosil Chiral-NR, eluent: heptane/ethanol+NH$_4$OAc (60:40), pressure: 18 bar; flow rate: 35 ml/min) to afford (1R)-N-[(3R)-2,6-dioxopiperidin-3-yl]-1,2,3,4-tetrahydronaphthalene-1-carboxamide (48 mg, white solid), retention time=43 min. MS (ISP): 287.1 ([M+H]$^+$).

Example 46

(1R)-N-[(3S)-2,6-Dioxopiperidin-3-yl]-1,2,3,4-tetrahydronaphthalene-1-carboxamide

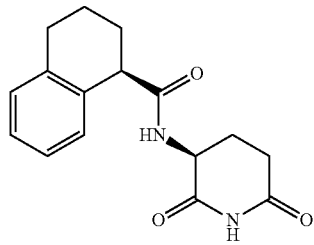 [SMILES: O=C1CC[C@H](NC(=O)[C@@H]2CCCc3ccccc32)C(=O)N1]

a) N-[(3S)-2,6-Dioxopiperidin-3-yl]-1,2,3,4-tetrahydronaphthalene-1-carboxamide (MIXTURE OF 2 EPIMERS)

The title compound was obtained in analogy to example 2 using (RS)-1,2,3,4-tetrahydronaphthalene-1-carboxylic acid[99] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 287.2 ([M+H]$^+$).

b) (1R)-N-[(3S)-2,6-Dioxopiperidin-3-yl]-1,2,3,4-tetrahydronaphthalene-1-carboxamide The epimers of N-[(3S)-2,6-dioxopiperidin-3-yl]-1,2,3,4-tetrahydronaphthalene-1-carboxamide (210 mg) from step a were separated using chiral HPLC (column: Reprosil Chiral-NR, eluent: heptane/ethanol+NH$_4$OAc (60:40), pressure: 18 bar; flow rate: 35 ml/min) to afford (1R)-N-[(3S)-2,6-dioxopiperidin-3-yl]-1,2,3,4-tetrahydronaphthalene-1-carboxamide (39 mg, white solid), retention time=44 min. MS (ISP): 287.1 ([M+H]$^+$).

Example 47

(S)-N-(2,6-Dioxopiperidin-3-yl)pyrazolo[1,5-a]pyridine-3-carboxamide

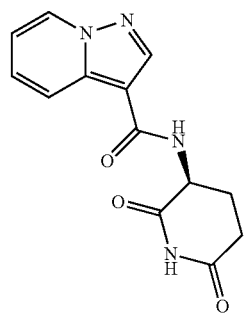 [SMILES: O=C1CC[C@H](NC(=O)c2cnn3ccccc23)C(=O)N1]

The title compound was obtained in analogy to example 2 using pyrazolo[1,5-a]pyridine-3-carboxylic acid[100] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 273.1 ([M+H]$^+$).

Example 48

(R)-N-(2,6-Dioxopiperidin-3-yl)pyrazolo[1,5-a]pyridine-3-carboxamide

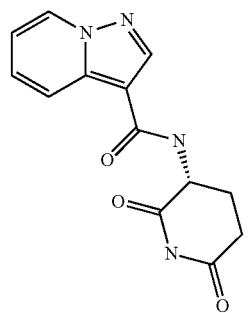 [SMILES: O=C1CC[C@@H](NC(=O)c2cnn3ccccc23)C(=O)N1]

The title compound was obtained in analogy to example 2 using pyrazolo[1,5-a]pyridine-3-carboxylic acid[100] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 273.1 ([M+H]$^+$).

Example 49

(R)-N-(2,6-Dioxopiperidin-3-yl)-1H-indazole-3-carboxamide

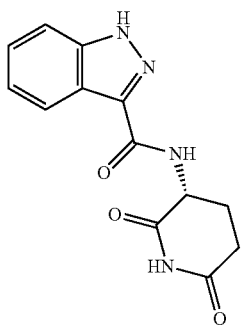 [SMILES: O=C1CC[C@@H](NC(=O)c2n[nH]c3ccccc23)C(=O)N1]

The title compound was obtained in analogy to example 2 using 1H-indazole-3-carboxylic acid[101] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 273.1 ([M+H]$^+$).

Example 50

(S)-N-(2,6-Dioxopiperidin-3-yl)imidazo[1,5-a]pyridine-3-carboxamide

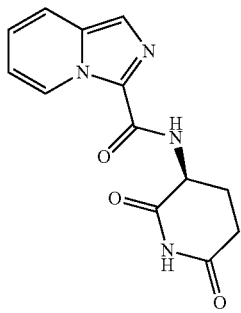 [SMILES: O=C1CC[C@H](NC(=O)c2ncc3ccccn23)C(=O)N1]

The title compound was obtained in analogy to example 2 using imidazo[1,5-a]pyridine-3-carboxylic acid[102] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 273.1 ([M+H]$^+$).

Example 51

(R)-N-(2,6-Dioxopiperidin-3-yl)imidazo[1,5-a]pyridine-3-carboxamide

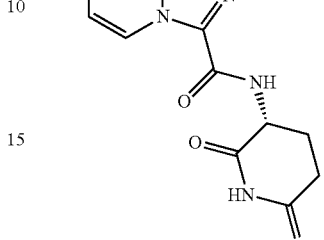

The title compound was obtained in analogy to example 2 using imidazo[1,5-a]pyridine-3-carboxylic acid[102] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 273.1 ([M+H]$^+$).

Example 52

(S)-N-(2,6-Dioxopiperidin-3-yl)indolizine-3-carboxamide

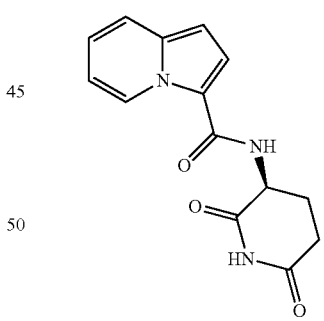

The title compound was obtained in analogy to example 2 using indolizine-3-carboxylic acid[103] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 272.1 ([M+H]$^+$).

Example 53

(R)-N-(2,6-Dioxopiperidin-3-yl)indolizine-3-carboxamide

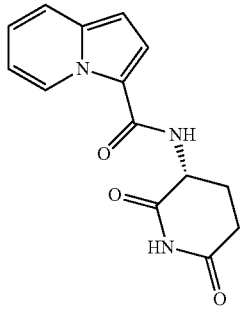 [SMILES: O=C1CC[C@@H](NC(=O)c2ccc3ccccn23)C(=O)N1]

The title compound was obtained in analogy to example 2 using indolizine-3-carboxylic acid[103] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 272.1 ([M+H]+).

Example 54

(S)-N-(2,6-Dioxopiperidin-3-yl)imidazo[1,2-a]pyridine-3-carboxamide

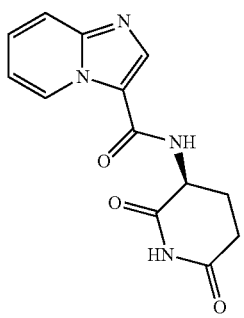 [SMILES: O=C1CC[C@H](NC(=O)c2cnc3ccccn23)C(=O)N1]

The title compound was obtained in analogy to example 2 using imidazo[1,2-a]pyridine-3-carboxylic acid[104] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 273.1 ([M+H]+).

Example 55

(R)-N-(2,6-Dioxopiperidin-3-yl)imidazo[1,2-a]pyridine-3-carboxamide

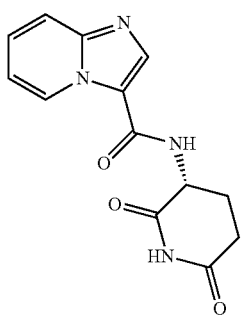 [SMILES: O=C1CC[C@@H](NC(=O)c2cnc3ccccn23)C(=O)N1]

The title compound was obtained in analogy to example 2 using imidazo[1,2-a]pyridine-3-carboxylic acid[104] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 273.1 ([M+H]+).

Example 56

(S)-N-(2,6-Dioxopiperidin-3-yl)pyrazolo[1,5-a]pyrimidine-3-carboxamide

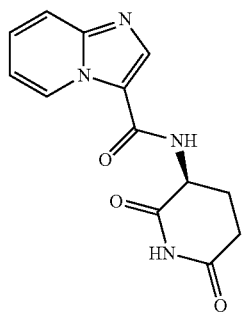 [SMILES: O=C1CC[C@H](NC(=O)c2cnc3ccccn23)C(=O)N1]

The title compound was obtained in analogy to example 2 using pyrazolo[1,5-a]pyrimidine-3-carboxylic acid[105] in place of 2,3-dihydro-1H-indene-1-carboxylic acid[75] and (3S)-3-aminopiperidine-2,6-dione hydrochloride[62] in place of 3-aminopiperidine-2,6-dione[60]. White solid. MS (ISP): 274.1 ([M+H]+).

Example 57

(R)-N-(2,6-Dioxopiperidin-3-yl)pyrazolo[1,5-a]pyrimidine-3-carboxamide

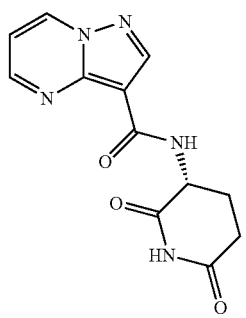 [SMILES: O=C1CC[C@@H](NC(=O)c2cnn3cccnc23)C(=O)N1]

The title compound was obtained in analogy to example 2 using pyrazolo[1,5-a]pyrimidine-3-carboxylic acid[105] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 274.1 ([M+H]+).

Example 58

N-(2,6-Dioxopiperidin-3-yl)-N-methylindoline-1-carboxamide

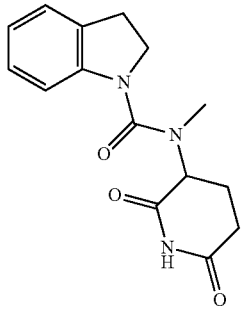 [SMILES: CN(C(=O)N1CCc2ccccc21)C1CCC(=O)NC1=O]

The title compound was obtained in analogy to example 9 using 3-(methylamino)piperidine-2,6-dione[65] in place of 3-aminopiperidine-2,6-dione[60]. Off-white solid. MS (ISP): 288.1 ([M+H]$^+$).

Example 59

(S)-N-(2,6-Dioxopiperidin-3-yl)-N-methylindoline-1-carboxamide

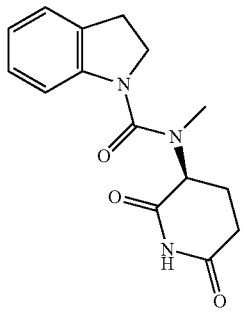 [SMILES: CN(C(=O)N1CCc2ccccc21)[C@H]1CCC(=O)NC1=O]

The epimers of N-(2,6-dioxopiperidin-3-yl)-N-methylindoline-1-carboxamide (120 mg) were separated using chiral HPLC (column: Reprosil Chiral-NR, eluent: heptane/ethanol+NH$_4$OAc (60:40), pressure: 18 bar; flow rate: 35 ml/min) to afford (S)-N-(2,6-dioxopiperidin-3-yl)-N-methylindoline-1-carboxamide (56 mg, off-white solid), retention time=12.4 min. MS (ISP): 288.1 ([M+H]$^+$).

Example 60

(R)-N-(2,6-Dioxopiperidin-3-yl)-N-methylindoline-1-carboxamide

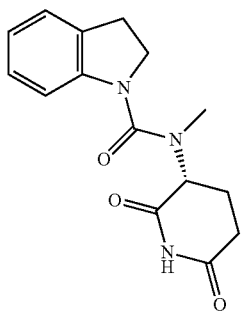 [SMILES: CN(C(=O)N1CCc2ccccc21)[C@@H]1CCC(=O)NC1=O]

The epimers of N-(2,6-dioxopiperidin-3-yl)-N-methylindoline-1-carboxamide (120 mg) were separated using chiral HPLC (column: Reprosil Chiral-NR, eluent: heptane/ethanol+NH$_4$OAc (60:40), pressure: 18 bar; flow rate: 35 ml/min) to afford (R)-N-(2,6-dioxopiperidin-3-yl)-N-methylindoline-1-carboxamide (52 mg, off-white solid), retention time=15.4 min. MS (ISP): 288.1 ([M+H]$^+$).

Example 61

(S)-N-(2,6-Dioxopiperidin-3-yl)-2-(pyridin-3-yl)acetamide

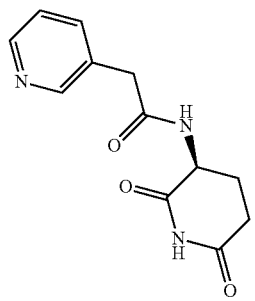 [SMILES: O=C1CC[C@H](NC(=O)Cc2cccnc2)C(=O)N1]

The title compound was obtained in analogy to example 2 using 2-(pyridin-3-yl)acetic acid[106] in place of 2,3-dihydro-1H-indene-1-carboxylic acid[75] and (3S)-3-aminopiperidine-2,6-dione[61] in place of 3-aminopiperidine-2,6-dione[60]. White solid. MS (ISP): 248.1 ([M+H]$^+$).

Example 62

N-(2,6-Dioxopiperidin-3-yl)-N-methyl-2,3-dihydro-1H-pyrrolo[2,3-b]pyridine-1-carboxamide

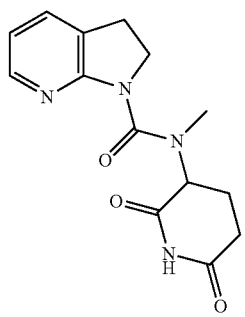

The title compound was obtained in analogy to example 9 using 2,3-dihydro-1H-pyrrolo[2,3-b]pyridine[91] in place of indoline and 3-(methylamino)piperidine-2,6-dione[65] in place of 3-aminopiperidine-2,6-dione[60]. Yellow solid. MS (ISP): 289.1 ([M+H]$^+$).

Example 63

(R)-N-(2,6-Dioxopiperidin-3-yl)-2-(pyridin-3-yl)acetamide

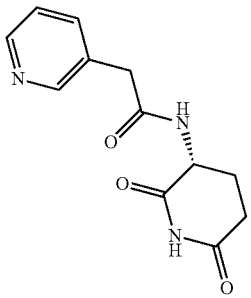 [SMILES: O=C1CC[C@@H](NC(=O)Cc2cccnc2)C(=O)N1]

The title compound was obtained in analogy to example 2 using 2-(pyridin-3-yl)acetic acid[106] in place of 2,3-dihydro-1H-indene-1-carboxylic acid[75] and (3R)-3-aminopiperidine-2,6-dione[63] in place of 3-aminopiperidine-2,6-dione[60]. Off-white solid. MS (ISP): 248.1 ([M+H]+).

Example 64

(R)-N-(2,6-Dioxopiperidin-3-yl)-3,4-dihydro-1,8-naphthyridine-1(2H)-carboxamide

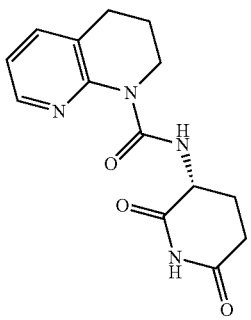 [SMILES: O=C1CC[C@@H](NC(=O)N2CCCc3cccnc32)C(=O)N1]

The title compound was obtained in analogy to example 9 using 1,2,3,4-tetrahydro-1,8-naphthyridine[92] in place of indoline and (R)-3-aminopiperidine-2,6-dione[63] in place of 3-aminopiperidine-2,6-dione[60]. White solid. MS (ISP): 289.1 ([M+H]+).

Example 65

(S)-2-(4-Acetamidophenyl)-N-(2,6-dioxopiperidin-3-yl)acetamide

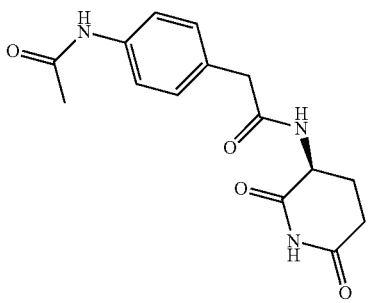 [SMILES: CC(=O)Nc1ccc(CC(=O)N[C@H]2CCC(=O)NC2=O)cc1]

The title compound was obtained in analogy to example 2 using 2-(4-acetamidophenyl)acetic acid[107] in place of 2,3-dihydro-1H-indene-1-carboxylic acid[75] and (3S)-3-aminopiperidine-2,6-dione[61] in place of 3-aminopiperidine-2,6-dione[60]. White solid. MS (ISP): 304.1 ([M+H]+).

Example 66

(R)-2-(4-Acetamidophenyl)-N-(2,6-dioxopiperidin-3-yl)acetamide

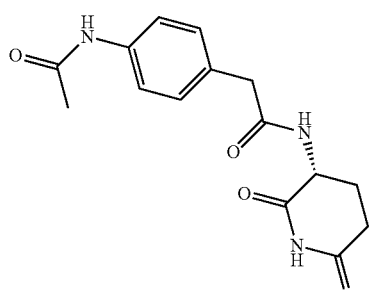

The title compound was obtained in analogy to example 2 using 2-(4-acetamidophenyl)acetic acid[107] in place of 2,3-dihydro-1H-indene-1-carboxylic acid[75] and (3R)-3-aminopiperidine-2,6-dione[63] in place of 3-aminopiperidine-2,6-dione[60]. Off-white solid. MS (ISP): 304.1 ([M+H]+).

Example 67

(R)-2-(3-Acetamidophenyl)-N-(2,6-dioxopiperidin-3-yl)acetamide

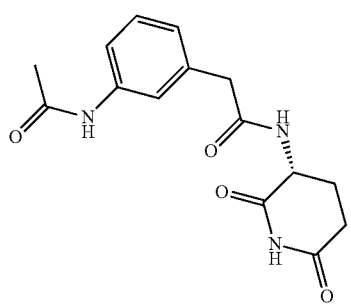 [SMILES: CC(=O)Nc1cccc(CC(=O)N[C@@H]2CCC(=O)NC2=O)c1]

The title compound was obtained in analogy to example 2 using 2-(3-acetamidophenyl)acetic acid[108] in place of 2,3-dihydro-1H-indene-1-carboxylic acid[75] and (3R)-3-aminopiperidine-2,6-dione[63] in place of 3-aminopiperidine-2,6-dione[60]. White solid. MS (ISP): 304.2 ([M+H]+).

Example 68

(S)-2-(3-Acetamidophenyl)-N-(2,6-dioxopiperidin-3-yl)acetamide

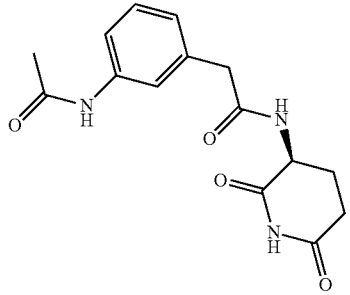 [SMILES: CC(=O)Nc1cccc(CC(=O)N[C@H]2CCC(=O)NC2=O)c1]

The title compound was obtained in analogy to example 2 using 2-(3-acetamidophenyl)acetic acid[108] in place of 2,3-dihydro-1H-indene-1-carboxylic acid[75] and (3S)-3-aminopiperidine-2,6-dione[61] in place of 3-aminopiperidine-2,6-dione[60]. White solid. MS (ISP): 304.1 ([M+H]$^+$).

Example 69

(S)-N-(2,6-Dioxopiperidin-3-yl)-2-(2-oxoindolin-5-yl)acetamide

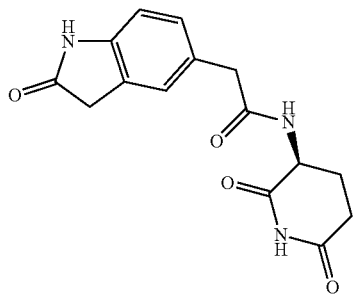 [SMILES: O=C1CC[C@H](NC(=O)Cc2ccc3c(c2)CC(=O)N3)C(=O)N1]

The title compound was obtained in analogy to example 2 using 2-(2-oxoindolin-6-yl)acetic acid[109] in place of 2,3-dihydro-1H-indene-1-carboxylic acid[75] and (3S)-3-aminopiperidine-2,6-dione[61] in place of 3-aminopiperidine-2,6-dione[60]. White solid. MS (ISP): 302.1 ([M+H]$^+$).

Example 70

(R)-N-(2,6-Dioxopiperidin-3-yl)-2-(2-oxoindolin-5-yl)acetamide

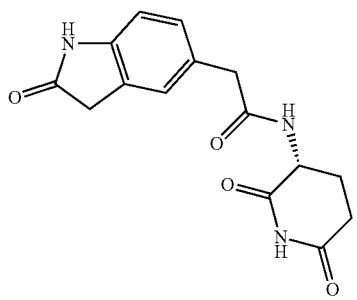 [SMILES: O=C1CC[C@@H](NC(=O)Cc2ccc3c(c2)CC(=O)N3)C(=O)N1]

The title compound was obtained in analogy to example 2 using 2-(2-oxoindolin-6-yl)acetic acid[109] in place of 2,3-dihydro-1H-indene-1-carboxylic acid[75] and (3R)-3-aminopiperidine-2,6-dione[63] in place of 3-aminopiperidine-2,6-dione[60]. White solid. MS (ISP): 302.1 ([M+H]$^+$).

Example 71 tert-Butyl (S)-3-((2,6-dioxopiperidin-3-yl)carbamoyl)-1-methyl-1,4,6,7-tetrahydro-5H-pyrazolo[4,3-c]pyridine-5-carboxylate

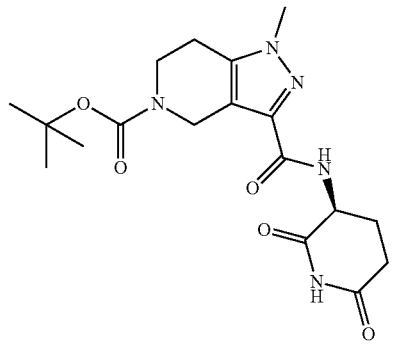 [SMILES: Cn1nc(C(=O)N[C@H]2CCC(=O)NC2=O)c2c1CCN(C(=O)OC(C)(C)C)C2]

To a mixture of (S)-3-aminopiperidine-2,6-dione hydrochloride[62] (54 mg) and 5-(tert-butoxycarbonyl)-1-methyl-4,5,6,7-tetrahydro-1H-pyrazolo[4,3-c]pyridine-3-carboxylic acid[110] (102 mg) were added a solution of HATU in N,N-dimethylformamide (1.1 ml, 0.358 M) and N,N-diisopropylethylamine (170 mg). The reaction mixture was shaken at 25° C. for 4 hours. The reaction mixture was then partitioned between water and a 1:1 mixture of ethyl acetate/THF. The organic layer was washed with brine, dried over Na$_2$SO$_4$, filtered and concentrated in vacuo. The crude material was purified by preparative HPLC followed by lyophilisation to afford tert-butyl (S)-3-((2,6-dioxopiperidin-3-yl)carbamoyl)-1-methyl-1,4,6,7-tetrahydro-5H-pyrazolo[4,3-c]pyridine-5-carboxylate (116 mg, 90.3%) as a white solid. MS (ISP): 392.4 ([M+H]$^+$).

Example 72

(S)-N-(2,6-Dioxopiperidin-3-yl)-1-methyl-4,5,6,7-tetrahydro-1H-pyrazolo[4,3-c]pyridine-3-carboxamide

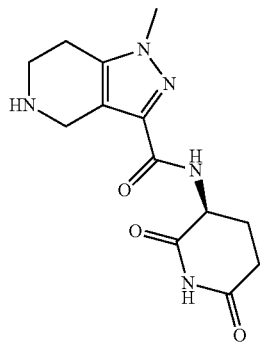 [SMILES: Cn1nc(C(=O)N[C@H]2CCC(=O)NC2=O)c2c1CCNC2]

To a stirred solution of tert-butyl (S)-3-((2,6-dioxopiperidin-3-yl)carbamoyl)-1-methyl-1,4,6,7-tetrahydro-5H-pyrazolo[4,3-c]pyridine-5-carboxylate (110 mg) in ethyl acetate (1 ml) was added a solution of 4 M HCl in dioxane (0.5 ml) The reaction mixture was stirred at 0° C. for 2 hours. The product was then collected by filtration, washed with ethyl acetate, and dried to afford (S)-N-(2,6-dioxopiperidin-3-yl)-

1-methyl-4,5,6,7-tetrahydro-1H-pyrazolo[4,3-c]pyridine-3-carboxamide (51 mg, 62.3%) as a white solid. MS (ISP): 292.3 ([M+H]+).

Example 73

(1S)-N-(1-Methyl-2,6-dioxopiperidin-3-yl)-1,2,3,4-tetrahydronaphthalene-1-carboxamide (1:1 MIXTURE OF EPIMERS)

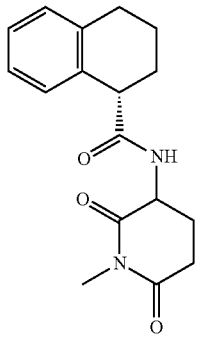

The title compound was obtained in analogy to example 2 using (S)-1,2,3,4-tetrahydronaphthoic acid in place of 2,3-dihydro-1H-indene-1-carboxylic acid[75] and 3-amino-1-methylpiperidine-2,6-dione hydrochloride[111] in place of 3-aminopiperidine-2,6-dione[60] White solid. MS (EI): 300.1 ([M+H]+).

Example 74

(1S)-N-(1-Methyl-2,6-dioxopiperidin-3-yl)-1,2,3,4-tetrahydronaphthalene-1-carboxamide (EPIMER 1)

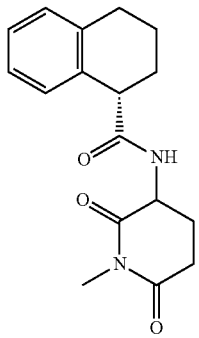

The epimers of (1S)-N-(1-methyl-2,6-dioxopiperidin-3-yl)-1,2,3,4-tetrahydronaphthalene-1-carboxamide (118 mg) were separated using chiral HPLC (column: Reprosil Chiral-NR, eluent: heptane/ethanol+NH4OAc (70:30), pressure: 18 bar; flow rate: 35 ml/min) to afford (1S)-N-(1-methyl-2,6-dioxopiperidin-3-yl)-1,2,3,4-tetrahydronaphthalene-1-carboxamide (EPIMER 1) (29 mg, white solid), retention time=37 min. MS (EI): 300.1 ([M+H]+).

Example -75

(1S)-N-(1-Methyl-2,6-dioxopiperidin-3-yl)-1,2,3,4-tetrahydronaphthalene-1-carboxamide (EPIMER 2)

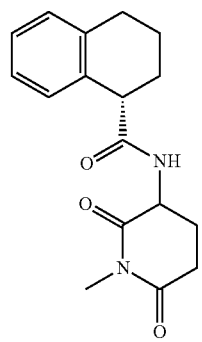 [SMILES: CN1C(=O)CCC(NC(=O)[C@H]2CCCc3ccccc32)C1=O]

The epimers of (1S)-N-(1-methyl-2,6-dioxopiperidin-3-yl)-1,2,3,4-tetrahydronaphthalene-1-carboxamide (118 mg) were separated using chiral HPLC (column: Reprosil Chiral-NR, eluent: heptane/ethanol+NH4OAc (70:30), pressure: 18 bar; flow rate: 35 ml/min) to afford (1S)-N-(1-methyl-2,6-dioxopiperidin-3-yl)-1,2,3,4-tetrahydronaphthalene-1-carboxamide (EPIMER 1) (29 mg, white solid), retention time=41 min. MS (EI): 300.1 ([M+H]+).

Example A (4S)-1-[6-[[2-[(9S)-7-(4-Chlorophenyl)-4,5,13-trimethyl-3-thia-1,8,11,12-tetrazatricyclo[8.3.0.02,6]trideca-2(6),4,7,10,12-pentaen-9-yl]acetyl]amino]hexanoyl]-N-[(3S)-2,6-dioxo-3-piperidyl]-3,4-dihydro-2H-quinoline-4-carboxamide

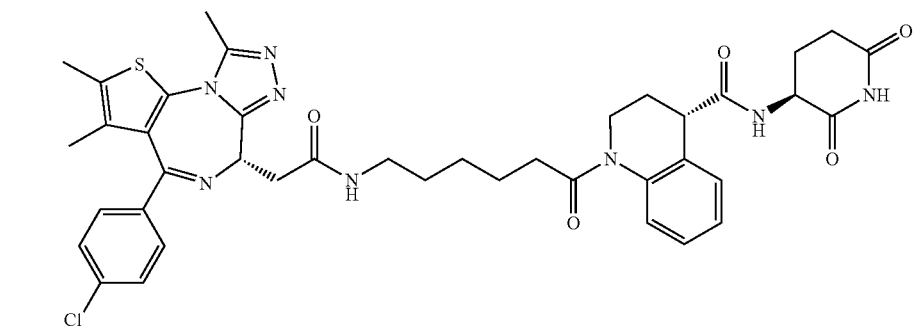 [SMILES: Cc1sc2c(c1C)C(c1ccc(Cl)cc1)=N[C@@H](CC(=O)NCCCCCC(=O)N1CC[C@H](C(=O)N[C@H]3CCC(=O)NC3=O)c3ccccc31)c1nnc(C)n1-2]

a) tert-Butyl N-[6-[(4S)-4-[[(3S)-2,6-dioxopiperidin-3-yl]carbamoyl]-3,4-dihydroquinolin-1(2H)-yl]-6-oxohexyl]carbamate To a stirred solution of 6-(tert-butoxycarbonylamino)hexanoic acid[112] (19.5 mg) in dichloromethane (0.4 ml) was added 1-chloro-N,N,2-trimethylpropenylamine (12.2 µl) at 0° C. After stirring for 20 min at room temperature, a solution of (4S)-N-[(3S)-2,6-dioxopiperidin-3-yl]-1,2,3,4-tetrahydroquinoline-4-carboxamide (22 mg, example 32) in dichloromethane (0.2 ml) was added dropwise followed by dropwise addition of N,N-diisopropylethylamine (33.4 µl). The solution was stirred at room temperature for 2 hours. The reaction mixture was partitioned between water and a 1:1 mixture of ethyl acetate and THF. The organic layer was washed with brine, dried over $Na_2SO_4$, filtered and concentrated in vacuo. The crude material was purified by flash chromatography (silica gel, 4 g, eluent: 0 to 5% of methanol in dichloromethane) to afford tert-butyl N-[6-[(4S)-4-[[(3S)-2,6-dioxopiperidin-3-yl]carbamoyl]-3,4-dihydroquinolin-1(2H)-yl]-6-oxohexyl]carbamate (36 mg, 94%) as an amorphous colourless solid. MS (ISP): 499.3 ([M+H]$^+$).

b) (4S)-1-(6-Aminohexanoyl)-N-[(3S)-2,6-dioxo-3-piperidyl]-3,4-dihydro-2H-quinoline-4-carboxamide Hydrochloride Salt To a stirred solution of tert-butyl N-[6-[(4S)-4-[[(3S)-2,6-dioxopiperidin-3-yl]carbamoyl]-3,4-dihydroquinolin-1(2H)-yl]-6-oxohexyl]carbamate (33 mg) in dichloromethane (1 ml) was added a 4 M solution of HCl in dioxane (412 µl). The reaction mixture was stirred at room temperature for 2 hours and was then evaporated to dryness. The residue was suspended in diethyl ether, sonicated, and filtered to afford (4S)-1-(6-aminohexanoyl)-N-[(3S)-2,6-dioxo-3-piperidyl]-3,4-dihydro-2H-quinoline-4-carboxamide hydrochloride salt (13 mg, 45%) which was used in the next step without further purification. MS (ISP): 401.3 ([M+H]$^+$).

c) (4S)-1-[6-[[2-[(9S)-7-(4-Chlorophenyl)-4,5,13-trimethyl-3-thia-1,8,11,12-tetrazatricyclo[8.3.0.02,6]trideca-2(6),4,7,10,12-pentaen-9-yl]acetyl]amino]hexanoyl]-N-[(3S)-2,6-dioxo-3-piperidyl]-3,4-dihydro-2H-quinoline-4-carboxamide To a stirred solution of (S)-2-(4-(4-chlorophenyl)-2,3,9-trimethyl-6H-thieno[3,2-f][1,2,4]triazolo[4,3-a][1,4]diazepin-6-yl)acetic acid[68] (13.1 mg), (4S)-1-(6-aminohexanoyl)-N-[(3S)-2,6-dioxo-3-piperidyl]-3,4-dihydro-2H-quinoline-4-carboxamide hydrochloride salt (13.0 mg) and N,N-diisopropylethylamine (20.8 µl) in DMF (0.5 ml) was added HATU (17 mg). The solution was stirred at room temperature for 2 hours. The reaction mixture was poured into a 1:1 mixture of ethyl acetate/THF and washed successively with water and brine. The organic layer was dried over $Na_2SO_4$, filtered, and concentrated in vacuo. The crude material was purified by flash chromatography (silica gel, 4 g, eluent: 0 to 10% of methanol in dichloromethane) to afford (4S)-1-[6-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]hexanoyl]-N-[(3S)-2,6-dioxo-3-piperidyl]-3,4-dihydro-2H-quinoline-4-carboxamide (15 mg, 64%) as a white solid. MS (ISP): 783.3 ([M+H]$^+$).

Example B (4S)-1-[6-[[2-[(9S)-7-(4-Chlorophenyl)-4,5,13-trimethyl-3-thia-1,8,11,12-tetrazatricyclo[8.3.0.02,6]trideca-2(6),4,7,10,12-pentaen-9-yl]acetyl]amino]hexanoyl]-N-[(3R)-2,6-dioxo-3-piperidyl]-3,4-dihydro-2H-quinoline-4-carboxamide

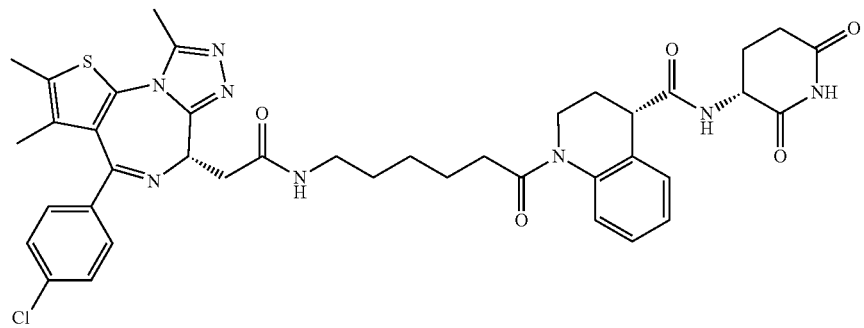 [SMILES: Cc1sc2c(c1C)C(c1ccc(Cl)cc1)=N[C@@H](CC(=O)NCCCCCC(=O)N1CC[C@H](C(=O)N[C@@H]3CCC(=O)NC3=O)c3ccccc31)c1nnc(C)n1-2]

a) N-[(3R)-2,6-dioxo-3-piperidyl]-1,2,3,4-tetrahydroquinoline-4-carboxamide (MIXTURE OF 2 EPIMERS)

The title compound was obtained in analogy to example 2 using (RS)-1,2,3,4-tetrahydroquinoline-4-carboxylic acid[94] in place of 2,3-dihydro-1H-indene-1-carboxylic acid[75] and (3R)-3-aminopiperidine-2,6-dione hydrochloride[64] in place of 3-aminopiperidine-2,6-dione[60]. White solid. MS (ISP): 288.3 ([M+H]$^+$).

b) (4S)-N-[(3R)-2,6-Dioxopiperidin-3-yl]-1,2,3,4-tetrahydroquinoline-4-carboxamide The epimers of N-[(3R)-2,6-dioxopiperidin-3-yl]-1,2,3,4-tetrahydroquinoline-4-carboxamide (110 mg) from step a were separated using chiral HPLC (column: Reprosil Chiral-NR, eluent: heptane/ethanol+NH$_4$OAc (60:40), pressure: 18 bar; flow rate: 35 ml/min) to afford (4S)-N-[(3R)-2,6-dioxopiperidin-3-yl]-1,2,3,4-tetrahydroquinoline-4-carboxamide (32 mg, white solid), retention time=39 min. MS (ISP): 288.1 ([M+H]$^+$).

c) tert-Butyl N-[6-[(4S)-4-[[(3R)-2,6-dioxopiperidin-3-yl]carbamoyl]-3,4-dihydroquinolin-1(2H)-yl]-6-oxohexyl]carbamate The title compound was obtained in analogy to example A using (4S)-N-[(3R)-2,6-dioxopiperidin-3-yl]-1,2,3,4-tetrahydroquinoline-4-carboxamide in place of (4S)-N-[(3S)-2,6-dioxopiperidin-3-yl]-1,2,3,4-tetrahydroquinoline-4-carboxamide in step a. Amorphous colourless solid. MS (ISP): 501.3 ([M+H]$^+$).

d) (4S)-1-(6-Aminohexanoyl)-N-[(3R)-2,6-dioxo-3-piperidyl]-3,4-dihydro-2H-quinoline-4-carboxamide Hydrochloride Salt The title compound was obtained in analogy to example A using tert-butyl N-[6-[(4S)-4-[[(3R)-2,6-dioxopiperidin-3-yl]carbamoyl]-3,4-dihydroquinolin-1(2H)-yl]-6-oxohexyl]carbamate in place of tert-butyl N-[6-[(4S)-4-[[(3S)-2,6-dioxopiperidin-3-yl]carbamoyl]-3,4-dihydroquinolin-1(2H)-yl]-6-oxohexyl]carbamate in step b. White solid. MS (ISP): 401.2 ([M+H]$^+$).

e) (4S)-1-[6-[[2-[(9S)-7-(4-Chlorophenyl)-4,5,13-trimethyl-3-thia-1,8,11,12-tetrazatricyclo[8.3.0.0$^{2,6}$]trideca-2(6),4,7,10,12-pentaen-9-yl]acetyl]amino]hexanoyl]-N-[(3R)-2,6-dioxo-3-piperidyl]-3,4-dihydro-2H-quinoline-4-carboxamide The title compound was obtained in analogy to example A using (4S)-1-(6-aminohexanoyl)-N-[(3R)-2,6-dioxo-3-piperidyl]-3,4-dihydro-2H-quinoline-4-carboxamide hydrochloride salt in place (4S)-1-(6-aminohexanoyl)-N-[(3S)-2,6-dioxo-3-piperidyl]-3,4-dihydro-2H-quinoline-4-carboxamide hydrochloride salt in step c. White solid. MS (ISP): 781.4 ([M+H]$^+$).

Example C (4R)-1-[2-[2-[2-[2-[[2-[(9S)-7-(4-Chlorophenyl)-4,5,13-trimethyl-3-thia-1,8,11,12-tetrazatricyclo[8.3.0.0$^{2,6}$]trideca-2(6),4,7,10,12-pentaen-9-yl]acetyl]amino]ethoxy]ethoxy]ethoxy]acetyl]-N-[(3S)-2,6-dioxo-3-piperidyl]-3,4-dihydro-2H-quinoline-4-carboxamide a) tert-Butyl N-[2-[2-[2-[2-[(4R)-4-[[(3S)-2,6-dioxopiperidin-3-yl]carbamoyl]-3,4-dihydroquinolin-1(2H)-yl]-2-oxoethoxy]ethoxy]ethoxy]ethyl]carbamate The title compound was obtained in analogy to example A using (4R)-N-[(3S)-2,6-dioxopiperidin-3-yl]-1,2,3,4-tetrahydroquinoline-4-carboxamide (example 33) in place of (4S)-N-[(3S)-2,6-dioxopiperidin-3-yl]-1,2,3,4-tetrahydroquinoline-4-carboxamide and 2,2-dimethyl-4-oxo-3,8,11,14-tetraoxa-5-azahexadecan-16-oic acid[113] in place of 6-(tert-butoxycarbonylamino)hexanoic acid in step a. Light yellow foam. MS (ISP): 577.5 ([M+H]$^+$).

b) (4R)-1-[2-[2-[2-(2-Aminoethoxy)ethoxy]ethoxy]acetyl]-N-[(3S)-2,6-dioxopiperidin-3-yl]-3,4-dihydro-2H-quinoline-4-carboxamide Hydrochloride Salt The title compound was obtained in analogy to example A using tert-butyl N-[2-[2-[2-[2-[(4R)-4-[[(3S)-2,6-dioxopiperidin-3-yl]carbamoyl]-3,4-dihydroquinolin-1(2H)-yl]-2-oxoethoxy]ethoxy]ethoxy]ethyl]carbamate in place of tert-butyl N-[6-[(4S)-4-[[(3S)-2,6-dioxopiperidin-3-yl]carbamoyl]-3,4-dihydroquinolin-1(2H)-yl]-6-oxohexyl]carbamate in step b. Light yellow solid. MS (ISP): 477.4 ([M+H]$^+$).

c) (4R)-1-[2-[2-[2-[2-[[2-[(9S)-7-(4-Chlorophenyl)-4,5,13-trimethyl-3-thia-1,8,11,12-tetrazatricyclo[8.3.0.0$^{2,6}$]trideca-2(6),4,7,10,12-pentaen-9-yl]acetyl]amino]ethoxy]ethoxy]ethoxy]acetyl]-N-[(3S)-2,6-dioxo-3-piperidyl]-3,4-dihydro-2H-quinoline-4-carboxamide The title compound was obtained in analogy to example A using (4R)-1-[2-[2-[2-(2-aminoethoxy)ethoxy]ethoxy]acetyl]-N-[(3S)-2,6-dioxopiperidin-3-yl]-3,4-dihydro-2H-quinoline-4-carboxamide hydrochloride salt in place of (4S)-1-(6-aminohexanoyl)-N-[(3S)-2,6-dioxo-3-piperidyl]-3,4-dihydro-2H-quinoline-4-carboxamide hydrochloride salt in step c. White solid. MS (ISP): 859.4 ([M+H]$^+$).

Although the foregoing invention has been described in some detail by way of illustration and example for purposes of clarity and understanding, it will be readily apparent to one of ordinary skill in the art in light of the teachings of this invention that certain changes and modifications may be

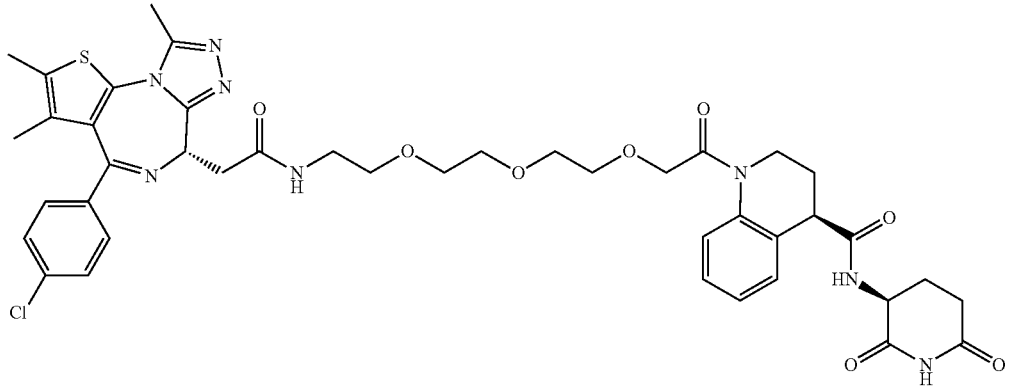 [SMILES: Cc1sc2c(c1C)C(c1ccc(Cl)cc1)=N[C@@H](CC(=O)NCCOCCOCCOCC(=O)N1CC[C@@H](C(=O)N[C@H]3CCC(=O)NC3=O)c3ccccc31)c1nnc(C)n1-2]

made thereto without departing from the spirit or scope of the invention as defined in the appended claims.

[1] Collins et al. *Biochem J.* 2017, 474(7), 1127-47
[2] WO2013020557
[3] WO2013063560
[4] WO 20131066432013106643n
[5] WO2015160845
[6] WO2016011906
[7] WO2016105518
[8] WO2017007612
[9] WO2017024318
[10] WO2017117473
[11] U.S. Pat. No. 4,558,057
[12] CN1696127
[13] Buckner et al. *Mayo Clinic Proceedings*, Dowden Health Media, Inc, USA, vol. 74, no. 2, 1 Feb. 1999(1999-02-01), pages 137-145
[14] Huang et al. *Zhongguo Yiyao Gongye Zazhi* 1993, 24(10), 437-41, 451
[15] Xu et al. *Zhongguo Yiyao Yao Gonge Zazhi* 1992, 23(6), 255-8
[16] Hendry et al. *Drugs under Experimental And Clinical Research* 1987, 13(Suppl. 1), 77-81
[17] WO2008007979
[18] CAS No. 1491860-78-6
[19] CAS No. 1480842-08-7
[20] CAS No. 1466257-08-8
[21] CAS No. 1465134-13-7
[22] CAS No. 1462991-23-6
[23] WO2017197051
[24] CAS No. 1487722-61-1
[25] CAS No. 1925250-20-9
[26] CAS No. 1512181-14-4
[27] CAS No. 1466882-97-2
[28] CAS No. 1468435-76-8
[29] CAS No. 1467495-41-5
[30] CAS No. 1480018-59-4
[31] CAS No. 1496032-76-8
[32] CAS No. 1993422-50-6
[33] CAS No. 1869440-20-9
[34] CAS No. 1495663-98-3
[35] CAS No. 1491860-78-6
[36] CAS No. 1485498-58-5
[37] CAS No. 1702002-20-7
[38] CAS No. 1490092-27
[39] CAS No. 1540138-47-3
[40] CAS No. 1998850-87-5
[41] CAS No. 1966549-05-2
[42] CAS No. 1957941-94-4
[43] CAS No. 1948185-02-1
[44] CAS No. 1925097-89-7
[45] CAS No. 1922676-64-9
[46] CAS No. 1923778-80-6
[47] CAS No. 1560748-55-1
[48] CAS No. 1559709-03-3
[49] CAS No. 1543949-7-7
[50] CAS No. 1541076-23-6
[51] CAS No. 1522124-94-2
[52] CAS No. 1519516-43-8
[53] CAS No. 1492524-17-0
[54] CAS No. 1491481-66-3
[55] CAS No. 1486311-15-2
[56] CAS No. 1467658-22-5
[57] CAS No. 1462942-69-3
[58] CAS No. 1464846-46-5
[59] CAS No. 1466763-16-5
[60] CAS No. 2353-44-8
[61] CAS No. 29883-25-8
[62] CAS No. 25181-50-4
[63] CAS No. 673485-72-8
[64] CAS No. 1801140-47-5
[65] CAS No. 1494409-88-9
[66] CAS No. 1268524-70-4
[67] Filippakopoulos, P. et al. *Nature* 2010, 468, 1067-1073
[68] CAS No. 202592-23-2
[69] CAS No. 26189-59-3
[70] *J. Chem. Soc., Chem. Commun.* 1979, 1180; *Org. Synth.* 1980, 59, 26-34
[71] Yen, H.-C. S., Xu, Q., Chou, D. M., Zhao, Z. & Elledge, S. J. Global Protein Stability Profiling in Mammalian Cells. *Science* 2008, 322, 918-923, doi:10.1126/science.1160489.
[72] Birdsall, B., King, R. W., Wheeler, M. R., Lewis, C. A. Jr, Goode, S. R., Dunlap, R. B. & Roberts, G. C. *Anal. Biochem.* 1983, 132, 353-361
[73] Eftink, *Methods Enzymol.* 1997, 278, 221-57
[74] CAS No. 91531-30-5
[75] CAS No. 14381-42-1
[76] CAS No. 221352-46-1
[77] CAS No. 123-38-6
[78] CAS No. 1463830-80-9
[79] CAS No. 1495903-25-7
[80] CAS No. 496-15-1
[81] CAS No. 91393-02-1
[82] CAS No. 1493112-18-7
[83] CAS No. 1482023-98-2
[84] CAS No. 1464854-51-0
[85] CAS No. 23357-47-3
[86] CAS No. 85977-52-2
[87] CAS No. 771-50-6
[88] CAS No. 1211516-10-7
[89] CAS No. 5381-25-9
[90] CAS No. 91-21-4
[91] CAS No. 10592-27-5
[92] CAS No. 13623-87-5
[93] CAS No. 357444-00-9
[94] CAS No. 13337-69-4
[95] CAS No. 26537-68-8
[96] CAS No. 933756-65-1
[97] CAS No. 20426-80-6
[98] CAS No. 773869-62-8
[99] CAS No. 1914-65-4
[100] CAS No. 16205-46-2
[101] CAS No. 4498-67-3
[102] CAS No. 1018587-80-8
[103] CAS No. 1259060-82-6
[104] CAS No. 6200-60-8
[105] CAS No. 25940-35-6
[106] CAS No. 501-81-5
[107] CAS No. 18699-02-0
[108] CAS No. 37777-54-1
[109] CAS No. 109737-08-8
[110] CAS No. 1306739-66-1
[111] CAS No. 1909304-98-8
[112] CAS No. 6404-29-1
[113] CAS No. 462100-06-7

We claim:

1. A compound of the formula:

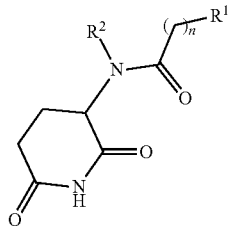

or a pharmaceutically acceptable salt thereof
wherein
$R^2$ is hydrogen or $C_1$-$C_6$alkyl;
$R^1$ is 2,3-dihydro-1H-pyrrolo[2,3-b]pyridinyl; and
n is 0 or 1.

2. The compound of claim 1, wherein $R^2$ is hydrogen.
3. The compound of claim 1, wherein $R^2$ is methyl.
4. The compound of claim 1 wherein n is 0.
5. The compound of claim 1, wherein n is 1.
6. The compound of claim 1 of the formula:

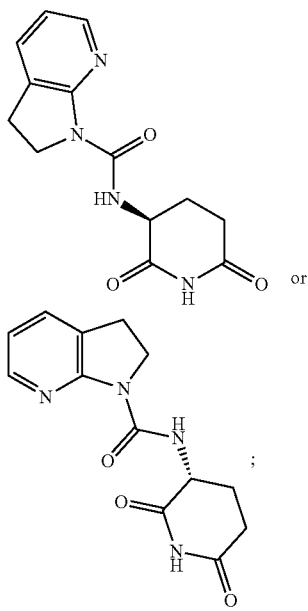

or a pharmaceutically acceptable salt thereof.

7. A pharmaceutical composition comprising a compound or pharmaceutically acceptable salt thereof of claim 1 optionally in a pharmaceutically acceptable carrier.

8. The compound of claim 6 of the formula:

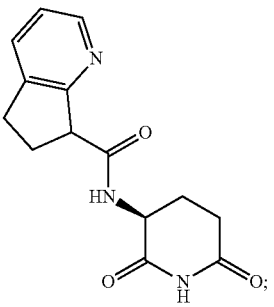 [SMILES: O=C1CC[C@H](NC(=O)C2CCc3cccnc32)C(=O)N1]

or a pharmaceutically acceptable salt thereof.

9. The compound of claim 6 of the formula:

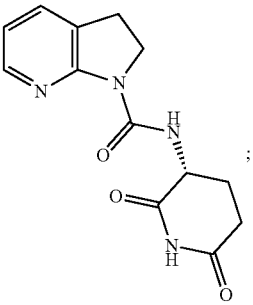 [SMILES: O=C1CC[C@@H](NC(=O)N2CCc3cccnc32)C(=O)N1]

or a pharmaceutically acceptable salt thereof.

* * * * *